United States Patent [19]
Klundt et al.

[11] Patent Number: 5,496,334
[45] Date of Patent: Mar. 5, 1996

[54] SUTURING APPARATUS

[75] Inventors: Kurt Klundt, Hirachhorn; Philipp Moll, Aachen; Georg Schlöndorff, Roetgen, all of Germany

[73] Assignee: J. Ströbel & Sohne GmbH & Co., München, Germany

[21] Appl. No.: 221,352

[22] Filed: Mar. 31, 1994

[30] Foreign Application Priority Data

Mar. 31, 1993 [DE] Germany .................. 43 10 555.6

[51] Int. Cl.$^6$ .................................................. A61B 17/04
[52] U.S. Cl. ..................... 606/145; 606/139; 606/144
[58] Field of Search .................... 606/139, 144–148, 606/175; 227/19, 88–90

[56] References Cited

U.S. PATENT DOCUMENTS

| | | | |
|---|---|---|---|
| 4,406,237 | 9/1983 | Eguchi et al. | 606/145 |
| 4,414,908 | 11/1983 | Eguchi et al. | 606/145 |
| 4,437,465 | 3/1984 | Nomoto et al. | |
| 4,440,171 | 4/1984 | Nomoto et al. | 606/145 |
| 4,465,070 | 8/1984 | Eguchi et al. | 606/145 |
| 4,747,358 | 5/1988 | Moll et al. | |
| 4,887,756 | 12/1989 | Puchy | 227/19 |
| 5,423,856 | 6/1995 | Green | 606/219 |

*Primary Examiner*—Gary Jackson

[57] ABSTRACT

A suturing apparatus to suture tissue edges to each other includes an oscillating needle and a loop catcher cooperating with the needle to form stitches. Two-legged forceps are provided to brace the tissue edges in the vicinity of the needle path transverse to the tissue edges. The forceps are movable to a closed position for holding together the tissue edges before the needle pierces them and, upon the ensuing exit of the needle from the tissue edges, an opened position to release the tissue edges. Furthermore, advancing tongs with two legs are provided for gripping the tissue edges directly on the other side of the forceps in a closed position and, in an open position, to release the tissue edges. The tongs are also shifted during each open phase of the forceps during a movement of the tissue in an advancement direction from an initial position into a closed position and, during each closed phase of the forceps, to their open position in a direction opposite the direction of advancement and back into the initial position.

58 Claims, 23 Drawing Sheets

5,496,334

SUTURING APPARATUS

BACKGROUND OF THE INVENTION

1. Field of the Invention

The present invention is directed to a suturing apparatus adapted to join edges of tissue using a single-thread overcast stitching operation.

2. Discussion of the Prior Art

A suturing apparatus is known as disclosed in U.S. Pat. No. 4,747,358 wherein two circular and rotatable discs press together tissues to be sutured. One of the discs is displaceable laterally, spring loaded toward the other disc and is driven stepwise in the direction of advancement of the tissue. The tissue is braced during suturing by two stationary support fingers, each extending on a respective side of two clamping discs so as to face a loop catcher along the periphery of either clamping disc in the direction of movement of the tissue and toward the path of motion of an oscillating needle. By this arrangement, the tissue edges to be sutured are held to the side when moving between the support fingers toward the path of the needle.

SUMMARY OF THE INVENTION

An object of the present invention is to provide an apparatus for suturing edges of tissue wherein the tissue edges to be sutured are held together during the suturing of the tissue edges in an improved manner.

This and other objects are achieved by providing an apparatus for suturing together tissue edges that includes an arc needle for repetitively piercing the tissue edges in order to suture the edges together, a loop catcher, an arrangement for oscillating the arc needle and the loop catcher through respective arcuate paths in a synchronized manner in order to form stitches and a bracing arrangement for securing the tissue edges during the stitching operation. The bracing arrangement includes forceps having first and second legs that are shifted, in synchronization with the oscillation of the arc needle, between a closed position wherein the first and second legs clamp the tissue edges to be sutured prior to the tissue edges being pierced by the arc needle and an open position wherein the first and second legs release the tissue edges following an ensuing exit of the arc needle from the tissue edges.

Additional objects and features of the invention will become more readily apparent from the following detailed description of preferred embodiments thereof when taken in conjunction with the drawings wherein like reference numerals refer to corresponding parts in the several views.

BRIEF DESCRIPTION OF THE DRAWINGS

FIG. 13 is a cross-sectional view taken along line XIII—XIII in FIG. 11a;

DETAILED DESCRIPTION OF THE PREFERRED EMBODIMENTS

Figure 1:
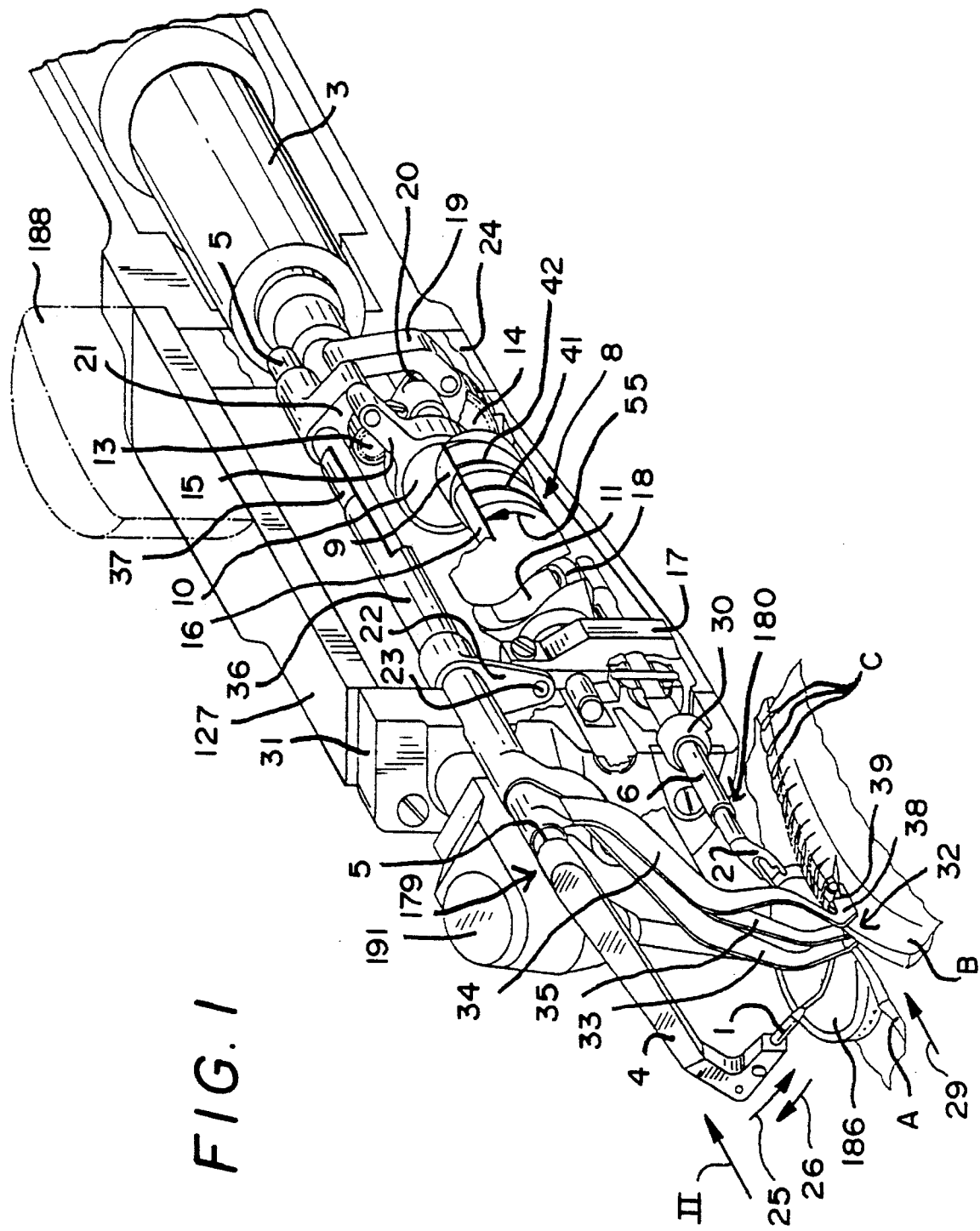
FIG. 1 is a partial perspective view of a first embodiment of the suturing apparatus of the invention.
Figure 2:
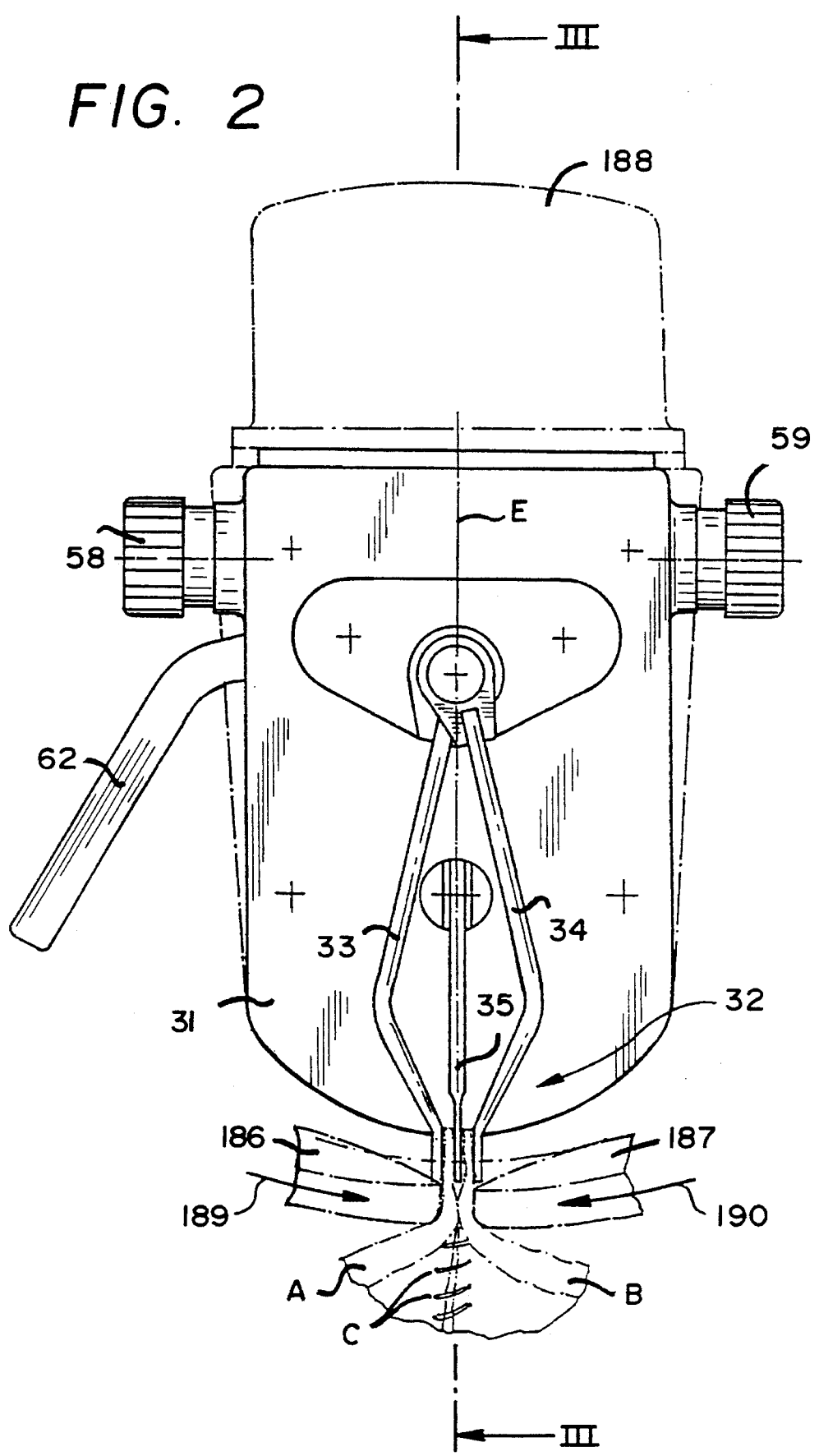
FIG. 2 is an enlarged view generally taken in the direction of arrow II of FIG. 1.

With initial reference to FIG. 1, the suturing apparatus of the present invention comprises an arc needle 1, a forked rocking gripper or loop catcher 2 and an electric DC motor 3 adapted to drive arc needle 1 and loop catcher 2. The arc needle I is mounted in a needle lever 4 radially projecting from a needle shaft 5. The loop catcher 2 is mounted on a gripper rod 6.

By means of reduction gearing 7, DC motor 3 drives a control roller 8 that is formed with a needle drive cam 9, a gripper drive cam 10 and a gripper drive channel 11. The reduction gearing 7 is constituted by a pinion 13 mounted on an output shaft 12 of DC motor 3 and by a gear 14 that is coaxial with and mounted on the control roller 8 and which meshes with pinion 13.

By means of a linkage (not shown) acting on a drive arm (also not shown) that radially projects from the needle shaft 5, needle drive cam 9 is interconnected with needle shaft 5. The gripper drive cam 10 cooperates with gripper rod 6 by means of a linkage 15, a pivot shaft 16 and a swivel plate 17. The gripper drive channel 11 receives a roller 18 rotatably supported on an end of the gripper rod 6 which is remote from loop catcher 2.

Linkage 15 is linked by a connection bracket 19 to a drive arm 20 radially projecting from pivot shaft 16. Linkage 15 is also connected to a guide arm 21 radially projecting from needle shaft 5 upon which guide arm 21 is rotatably mounted. Swivel plate 17 is suspended from a support arm 22 projecting radially from needle shaft 5. Swivel plate 17 is freely rotatable relative to needle shaft 5 and includes a bore (not labeled) that receives a support bolt 23 extending parallel to needle shaft 5.

Needle shaft 5 and pivot shaft 16 are parallel to each other, extend in the longitudinal direction of the apparatus and are rotatably supported in a housing 24. Control roller 8 and its associated gear 14 are rotatably supported on pivot shaft 16 between swivel plate 17 and connection bracket 19. As also clearly shown in FIG. 1, output shaft 12 of DC motor 3 is parallel to needle shaft 5 and pivot shaft 16.

The suturing apparatus of the present invention is intended to be used to suture tissue edges together, for instance, two tissue edges A, B. In the process, arc needle 1 oscillates to-and-fro in the direction of arrows 25, 26; loop catcher 2 rocks in the direction of arrows 27, 28 in order to cooperate with arc needle 1 for the purpose of forming stitches; and tissue edges A, B are jointly advanced in a stepwise manner in the direction of arrow 29 in order to produce single-thread overcast stitching C. Gripper rod 6 is rotatably supported and axially displaceably mounted to a ball joint 30 which, in turn, is supported in the front wall 31 of housing 24 for universal pivoting movement.

The suturing apparatus of the invention further comprises forceps 32 adapted to brace the tissue edges A, B in the vicinity of the path of arc needle 1 running transversely through edges A, B when being sutured together. Forceps 32 are adapted to open and close synchronously with the movement of the arc needle 1 and comprise a right leg 33 and a left leg 34. The two forceps legs 33, 34 are mounted on opposing sides of a stationary middle arm 35 that projects forward from front wall 31 and are pivoted to a closed position prior to each piercing of the tissue edges A, B by arc needle 1 in order to press the tissue edges A, B together, namely the tissue edge A against one side of middle arm 35 and the other tissue edge B against the other side of middle arm 35. Following the ensuing exit of arc needle 1 from tissue edges A, B, legs 33, 34 are pivoted to an open position so as to release tissue edges A, B.

More specifically, the right forceps leg 33 projects essentially radially from the front end of a hollow outer shaft 36 and the left forceps leg 34 projects from the front end of a hollow inner shaft 37 passing through hollow outer shaft 36. Hollow inner shaft 37 receives needle shaft 5. In this manner, hollow inner shaft 37 is rotatably supported by needle shaft 5 and hollow outer shaft 36 is rotatably supported by inner shaft 37. In turn, needle shaft 5 is rotatably supported by means of the mounting of hollow inner shaft 37 and hollow outer shaft 36 in front wall 31. Support arm 22 for swivel plate 17, that functions to shift loop catcher 2, is rotatably supported upon outer shaft 36 inside of housing shaft 24 adjacent front wall 31.

Figure 3:
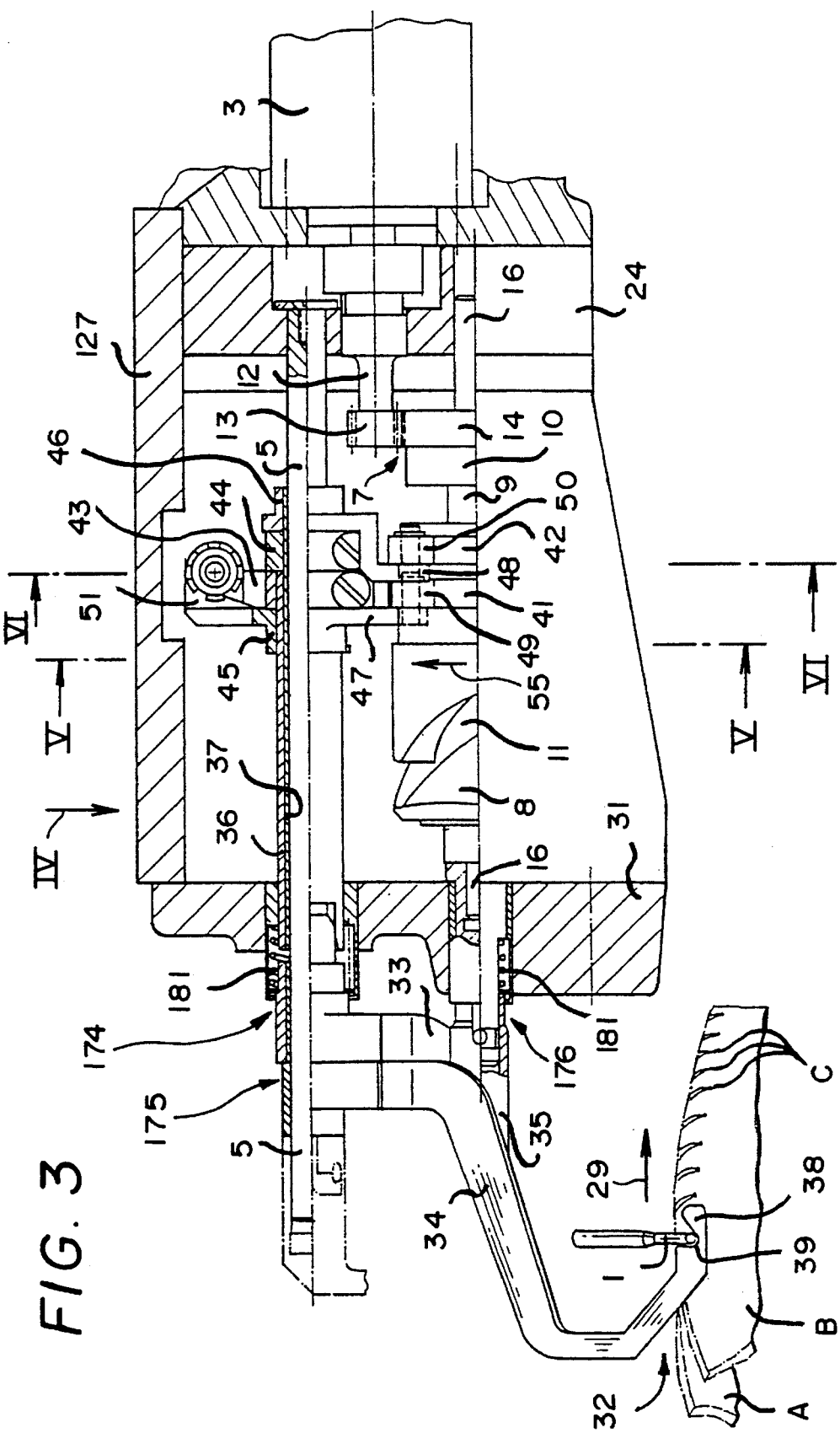
FIG. 3 is a cross-sectional view generally taken along line III—III of FIG. 2 shown on another scale.
Figure 4:
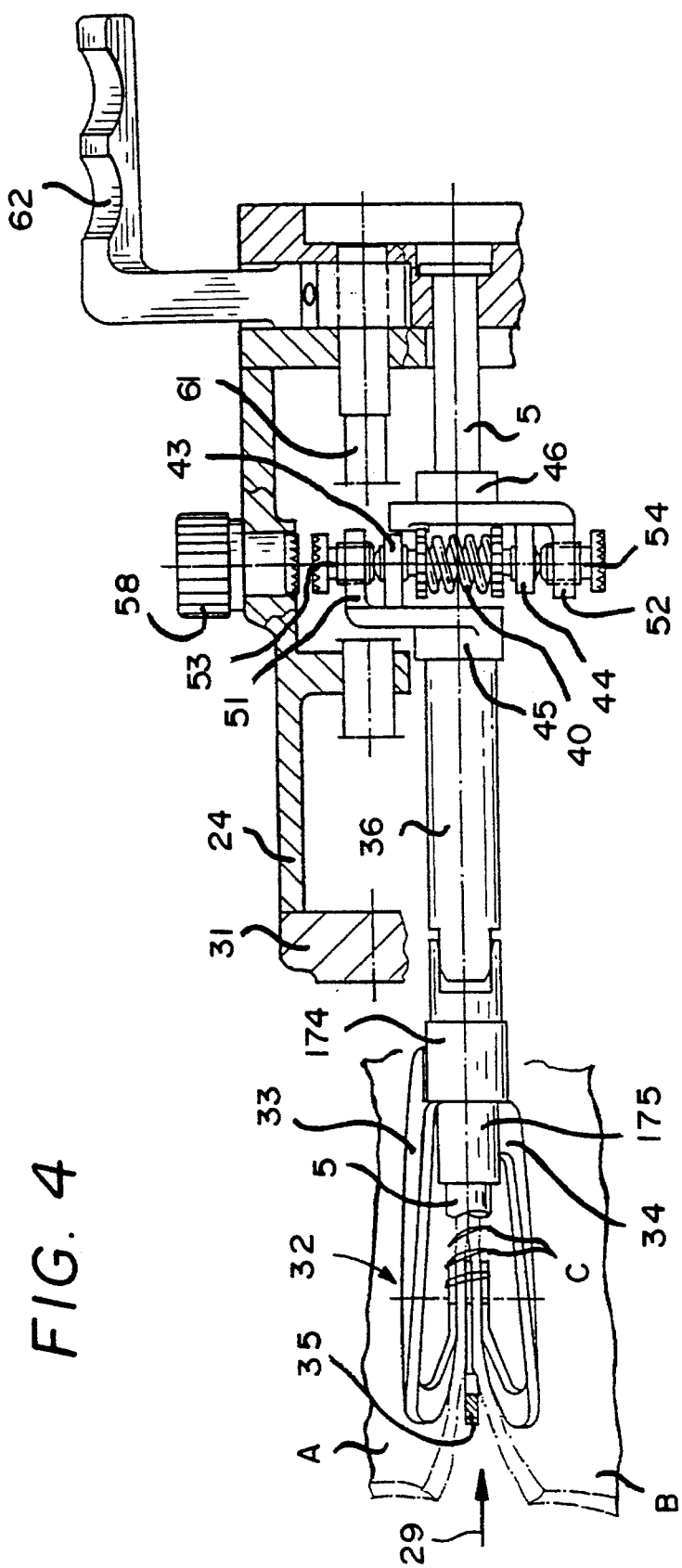
FIG. 4 is a view taken in the direction of arrow IV of FIG. 3 showing the apparatus with a cover removed.
Figure 5:
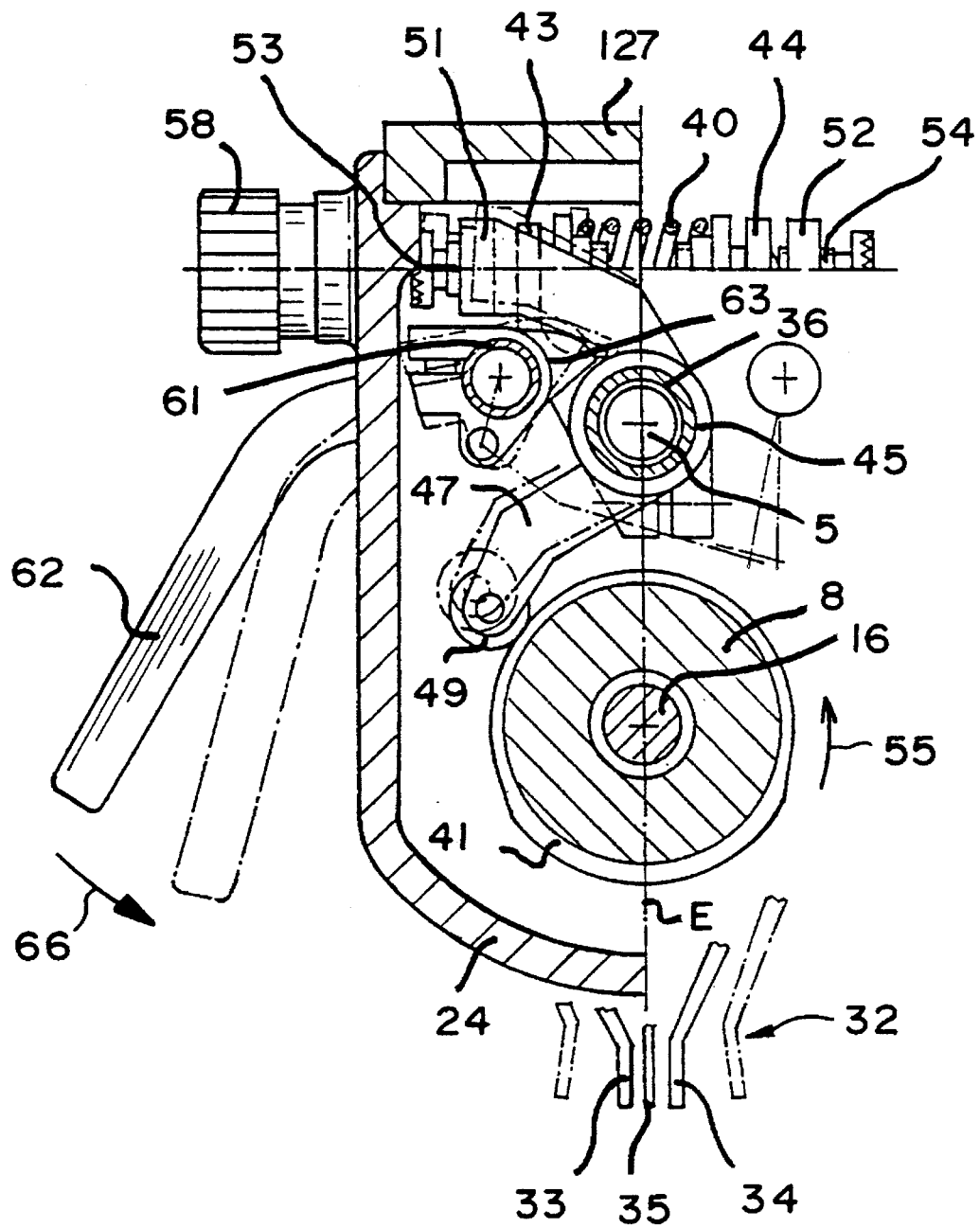
FIG. 5 is a cross-sectional view taken along line V—V of FIG. 3 but on the scale of FIG. 2.

Each of right forceps leg 33, left forceps leg 34 and stationary middle arm 35 comprises at its respective free end a planar presser foot 38 adapted to engage tissue edge A, tissue edge B or both tissue edges A, B respectively. Each presser foot 38 is formed with a recessed portion 39 through which arc needle is adapted to pass as clearly shown in FIGS. 1 and 3.

With regards to the forceps 32 incorporated in the embodiment of FIGS. 1–8, right leg 33 and left leg 34 are biased by a common helical compression spring 40 into their closed positions but can be pivoted into open positions against the loading force of spring 40 by means of respective control cams 41 and 42 formed in control roller 8. The helical compression spring 40 is mounted between first drive levers 43, 44 of the right and left forceps legs 33, 34. First drive levers 43, 44 project substantially radially from respective rear ends of outer shaft 36 and inner shaft 37 and cooperate through respective second drive levers 45 and 46 with control cams 41 and 42 for the right forceps leg 33 and the left forceps leg 34. The two second drive levers 45, 46 are rotatably supported on the outer and inner shafts 36, 37 respectively and are formed with radially projecting arms 47, 48 each of which is adapted to rest by means of a roller 49, 50 against a respective control cam 41, 42. Additional radially projecting arms 51, 52 extend on the side of first drive levers 43, 44 which is away from helical compression spring 40 and a pressure pin 53, 54 is screwed into each arm 51, 52 while also externally resting against an associated first drive lever 43, 44.

Figure 6:
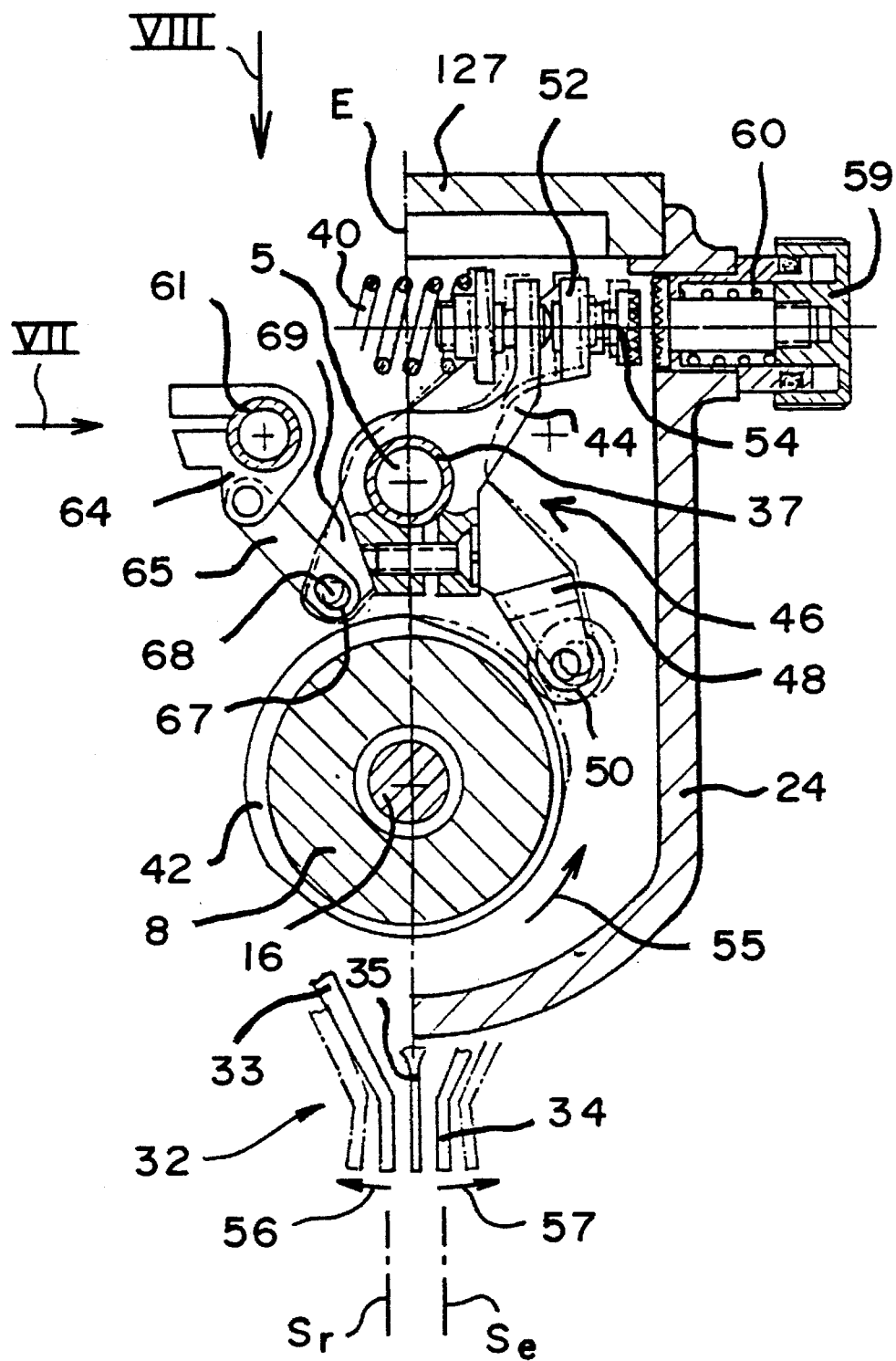
FIG. 6 is a cross-sectional view taken along line VI—VI of FIG. 3 but on the scale of FIG. 2.
Figure 7:
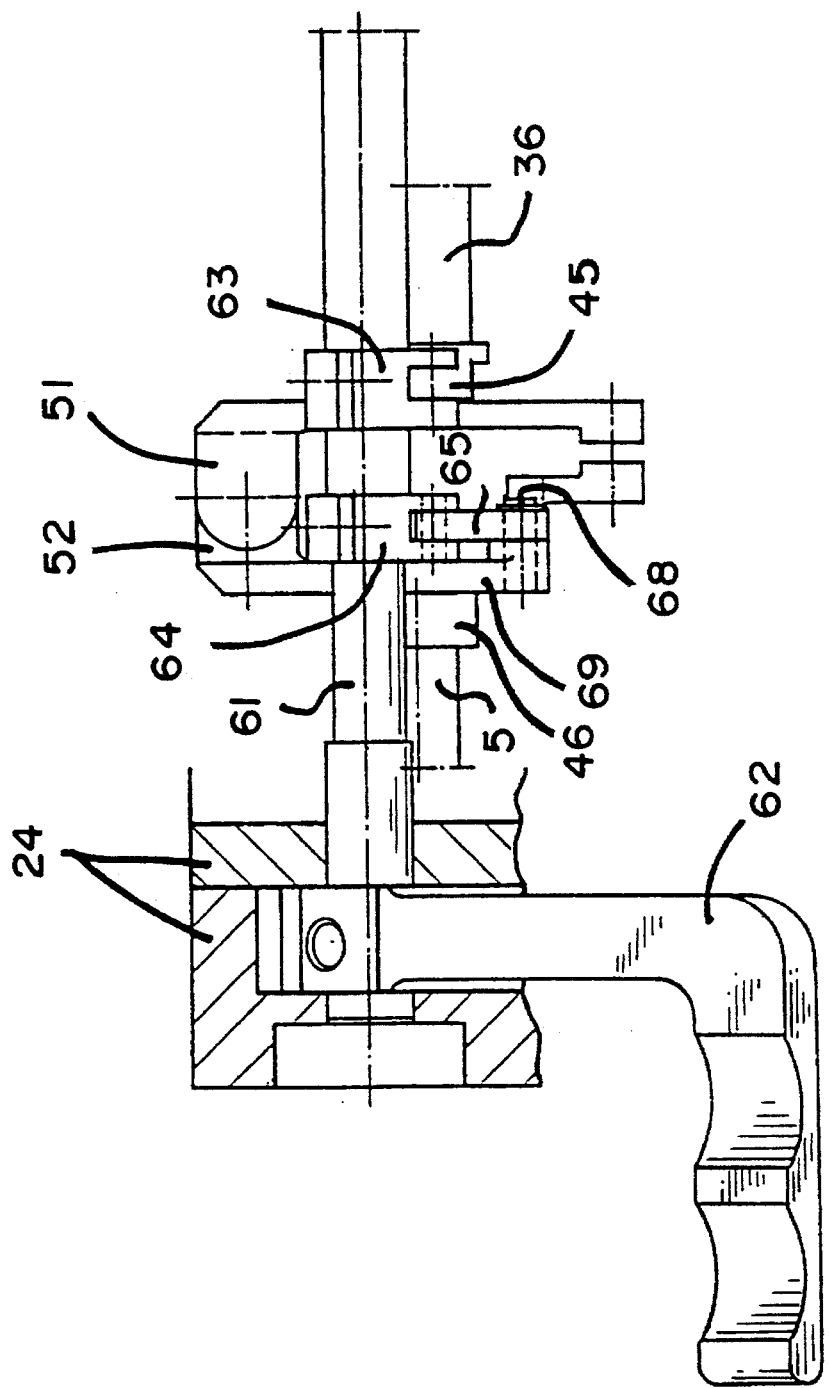
FIG. 7 is a side view taken in the direction of arrow VII in FIG. 6.
Figure 8:
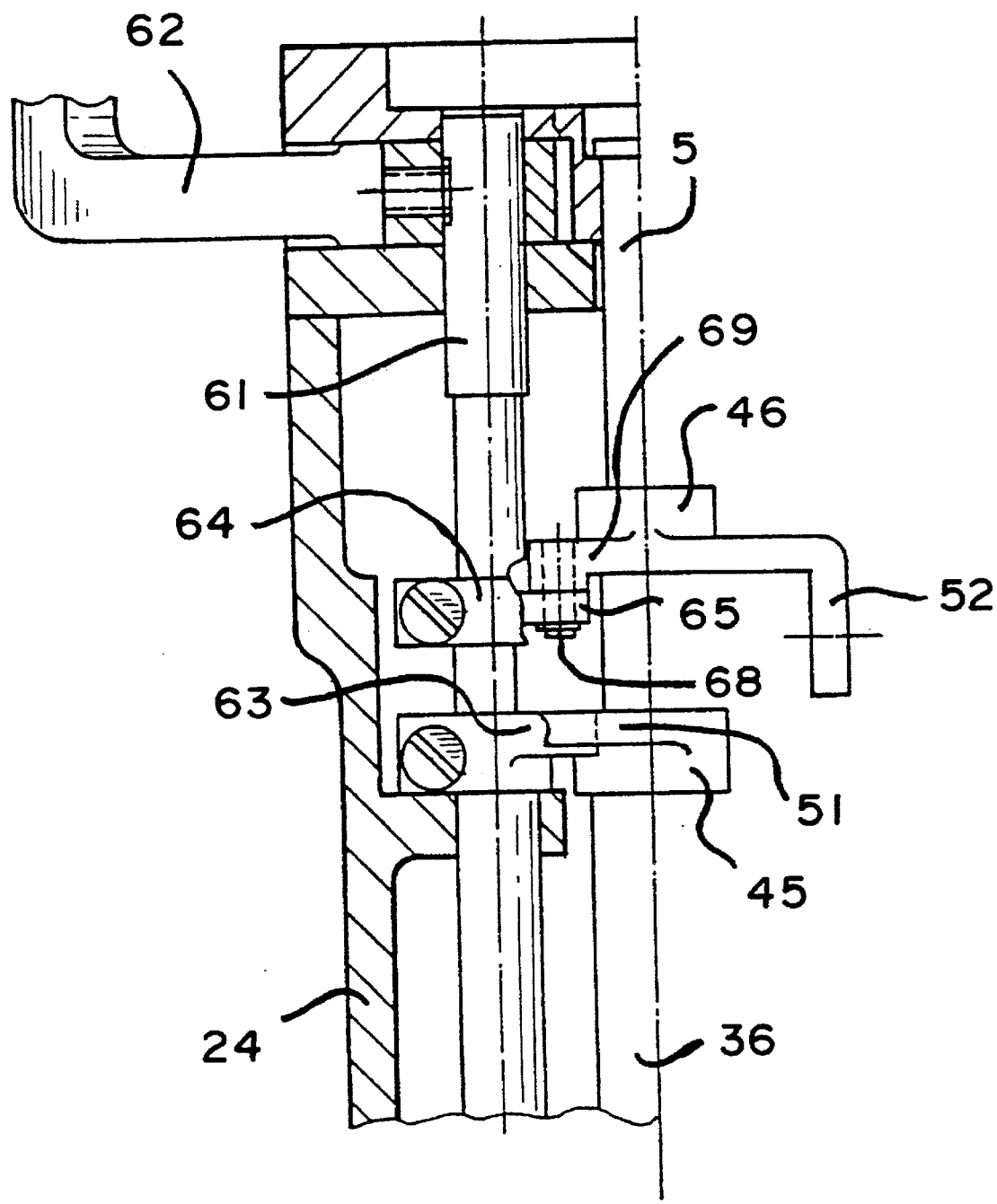
FIG. 8 is a top view taken in the direction of arrow VIII in FIG. 6.
Figure 9:
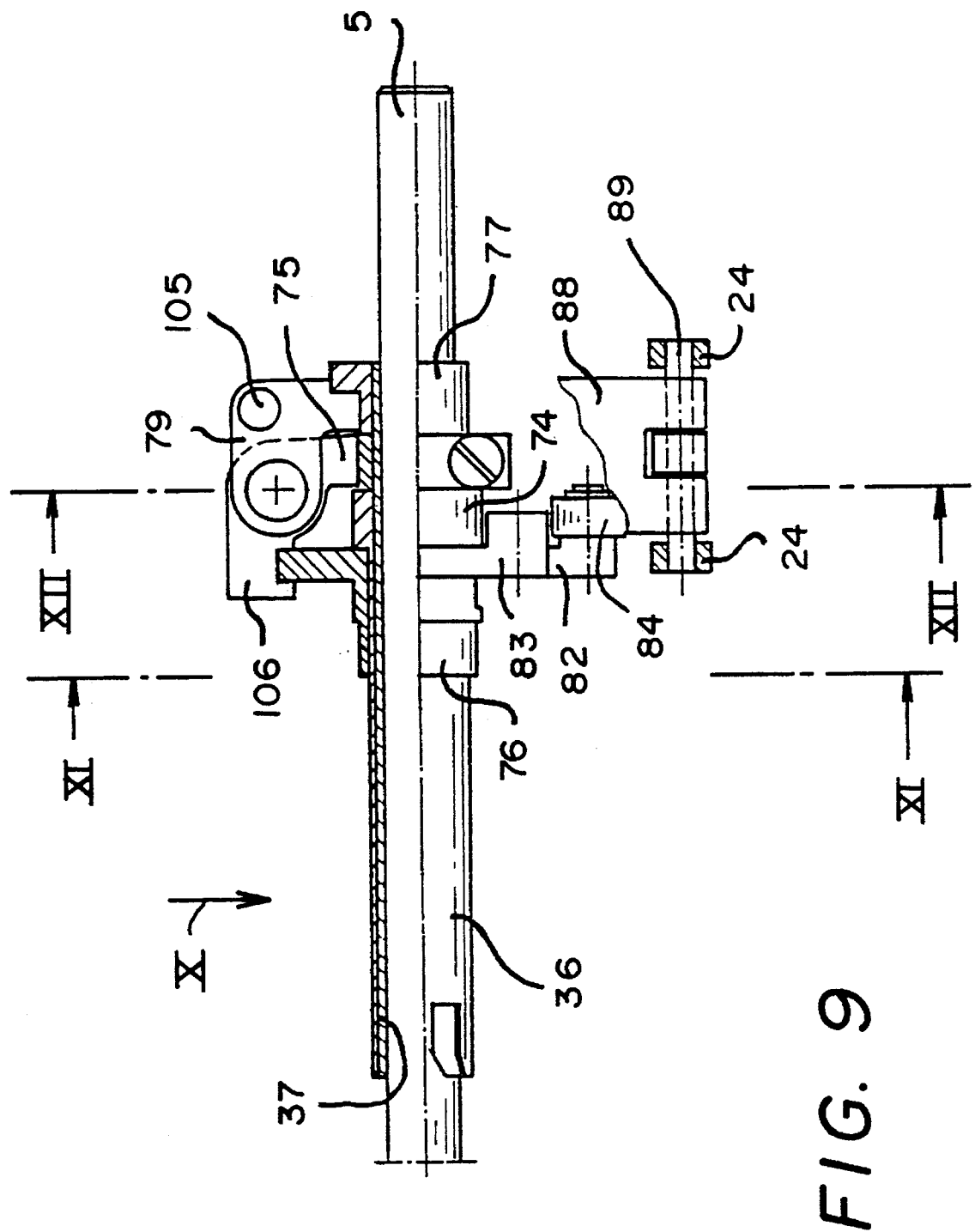
FIG. 9 is an enlarged cross-sectional view depicting a portion of the suturing apparatus similar to that shown in FIG. 3 but according to a second embodiment of the invention.
Figure 10:
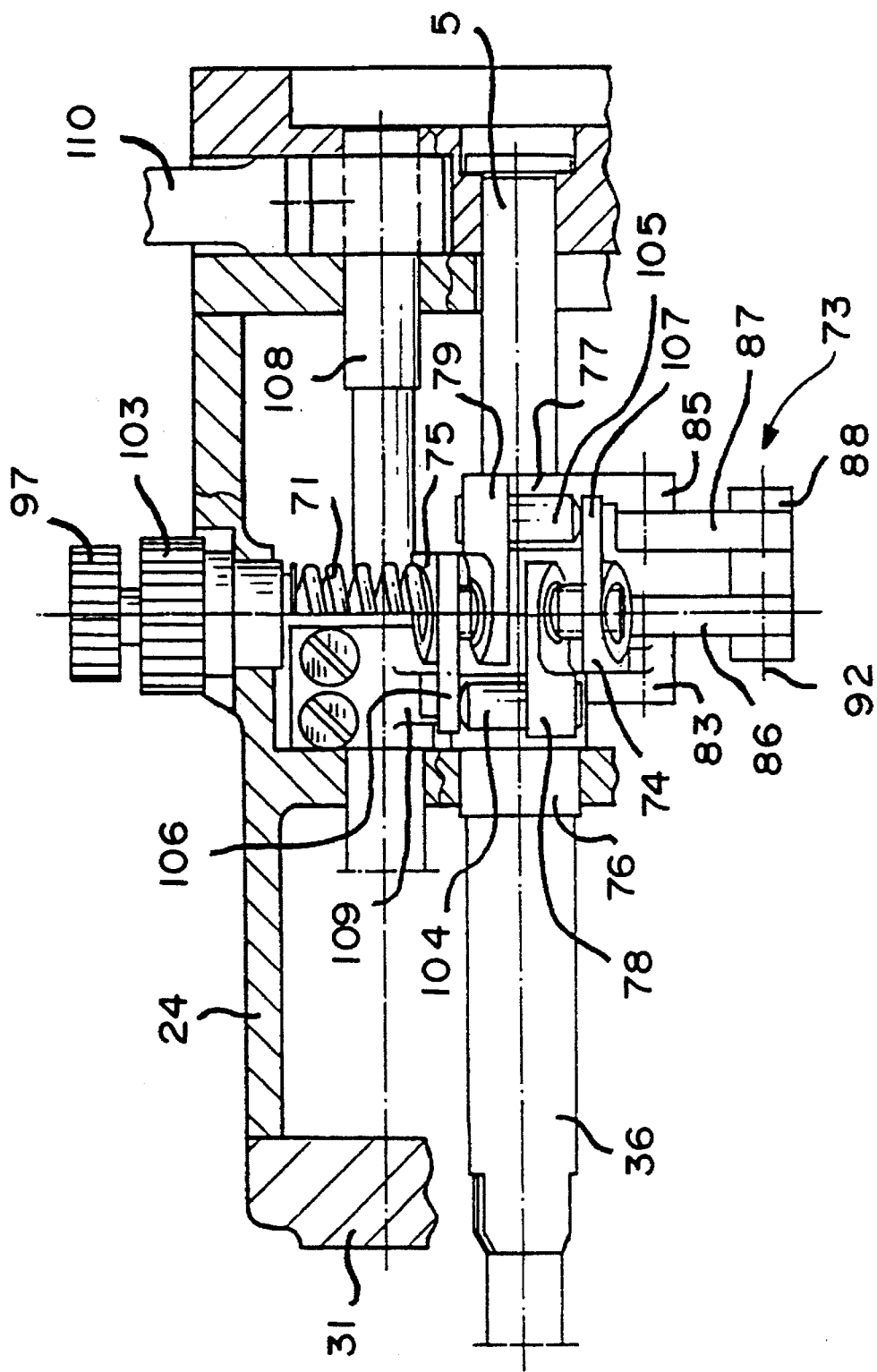
FIG. 10 is a top view taken in the direction of arrow X in FIG. 9.

With regards to FIGS. 1–8, legs 33, 34 of forceps 32 are in the closed position from which they will be pivoted, upon the rotation of control roller 8 in the direction of arrow 55 by control cams 41, 42, into the open position shown by dash lines in FIG. 6, i.e., in the direction of arrows 56, 57. The control cams 41, 42 are designed in such a manner that forceps legs 33, 34 carry out identical motions in the directions of arrows 56, 57. The second drive levers 45, 46 and first drive levers 43, 44 are also pivoted through identical angles in opposite directions. The particular position $S_r$, $S_l$ respectively assumed by the right and left forceps legs 33 and 34 in the closed position of FIG. 6 can be changed and adjusted using the associated pressure pins 53 and 54. For example, when pressure pin 53 in arm 51 of second drive lever 45 of right forceps leg 33 is screwed inward, its distance from stationary middle arm 35 will increase, and the distance will decrease when pressure pin 53 in arm 51 is screwed outward. The screwing motion of pressure pin 54 in arm 52 of second drive lever 46 of left forceps leg 34 causes a corresponding adjustment in the distance from stationary middle arm 35.

The screwing motion of each pressure pin 53, 54 is performed by means of drive knobs 58, 59 which must be pushed against the force of a helical compression spring 60 in order to link it to its respective pressure pin 53, 54.

In order to permit the insertion of tissue edges A, B prior to suturing into the suturing apparatus of FIG. 1 and to remove them following suturing, forceps 32 must be lifted. This motion is implemented through an actuator shaft 61 that extends parallel to outer and inner shafts 36 and 37 and which is rotatably supported inside housing 24, a handcrank 62 projecting outward from housing 24, an essentially radially extending projection 63 and an essentially radially projecting arm 64. Projection 63 directly cooperates with second drive lever 45 of right forceps leg 33 and arm 64 cooperates by means of a pressure bracket 65 with second drive lever 46 of left forceps leg 34 such that, when handcrank 62 is pivoted from the rest position shown in solid lines in FIG. 5 into the lifted position shown therein in dashed lines with a corresponding rotation of actuator shaft 61 in the direction of arrow 66, the two forceps legs 33, 34 will spread apart against the force exerted by helical-compression spring 40, whereby legs 33, 34 assume the lifted position indicted by dash lines in FIG. 5. The compression bracket 65 is linked to arm 64 and includes an elongated slot 67 at its other end. Slot 67 is engaged by a pin 68 of a third, substantially radial arm 69 of second drive lever 46 of left forceps leg 34. Elongated slot 67 allows pivoting to-and-fro of second drive lever 46 as associated control cam 42 rotates without, however, affecting actuator shaft 61 when handcrank 62 is in the rest position.

With regards to forceps 32 of FIGS. 9–15, right and left forceps legs 33 and 34 are each spring loaded by a respective helical compression spring 70 and 71 into the closed position, however, right and left forceps legs 33 and 34 are displaceable by a single control cam 72 provided on control roller 8, against the biasing force of springs 70 and 71, into the open position. Forceps legs 33, 34 are connected to each other by a linkage 73. The prestressing of helical compression spring 70 of right forceps leg 33 and its position $S_r$ assumed in the closed position when there is no tissue edges in the suturing apparatus can be changed and adjusted independently of one another. This also applies to the prestressing of helical compression spring 71 of left forceps leg 34 and its closed position $S_l$. Special steps have been taken such that the angles of pivoting of the forceps legs 33, 34 between the closed and open positions depend on the set closed positions $S_r$, $S_l$. These angles increase as the distances between the forceps legs 33, 34 in the closed positions $S_r$, $S_l$ from the stationary middle arm 35 become larger. This feature is advantageous concerning the properties of the tissue edges to be sutured, in particular their elasticity, to achieve reliable and yet gentle joining of the tissue edges in the closed position and full release in the open position of the forceps legs 33, 34.

The two helical compression springs 70, 71 are mounted outside two drive levers 74, 75 for right and left forceps legs 33 and 34 respectively. Drive levers 74, 75 essentially project radially from respective rear ends of outer shaft 36 and inner shaft 37 and, by means of second drive levers 76 and 77, cooperate with control cam 72 and linkage 73.

Each of the two drive levers 76, 77 is rotatably supported on the outer and inner shafts 36 and 37 respectively and fitted with an essentially radially projecting arm 78, 79 extending on a side of the associated first drive lever 74 which is away from the helical compression spring 70 of right forceps leg 33 and on a side of the associated first drive lever 75 which is away from helical compression spring 71 of left forceps leg 34. Pressure pins 80 and 81 rest externally against arms 78 and 79 and are screwed into a respective first drive lever 74 and 75. Furthermore, second drive lever 76 of right forceps leg 33 comprises two substantially radially projecting arms 82, 83 which, by means of a roller 84, are freely rotatably mounted and rest against control cam 72 or linkage 73. Second drive lever 77 of left forceps leg 34 is also fitted with a substantially radially projecting arm 85 for linkage 73.

Linkage arms 83, 85 are respectively connected by means of connection brackets 86 and 87 to one end of a pivot lever 88 that is connected at its other end to housing 24 so as to pivot about a shaft 89 parallel to outer and inner shafts 36 and 37. Pivot shaft 90, 91 between each connection bracket 86, 87 and associated linkage arm 83, 85 and pivot shaft 92 between the two connection brackets 86, 87 and pivot lever 88 run parallel to the outer and inner shafts 36 and 37. Linkage arms 83, 85 and connection brackets 86, 87, as well as pivot lever 88, actually constitute linkage 73. They are designed and mounted in such a manner that the two drive levers 76, 77 can only assume mirror-symmetrical positions relative to a plane of symmetry E in the manner illustrated by FIGS. 11a and 11b.

Figure 11A:
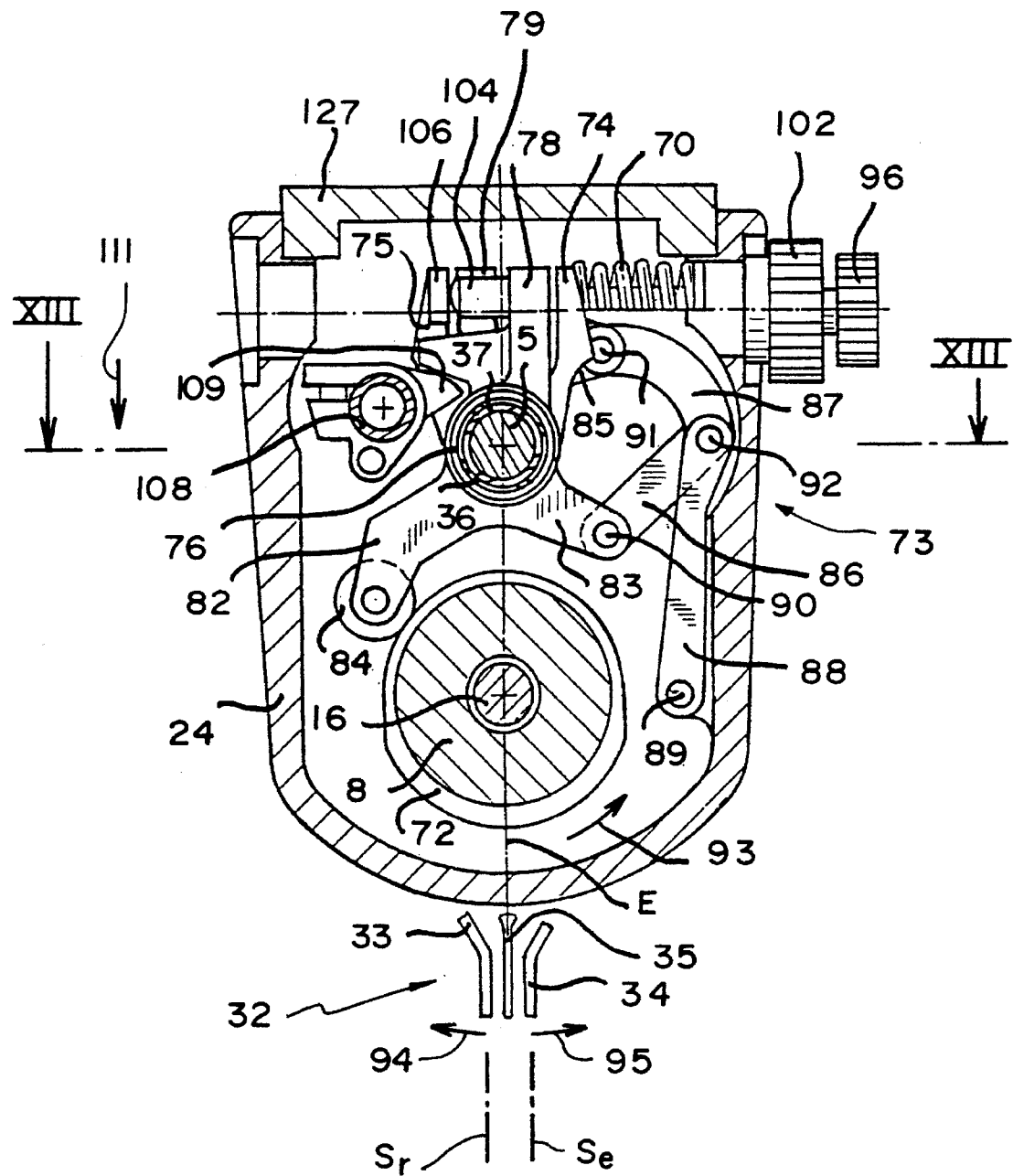
FIG. 11a is a cross-sectional view taken along line XI—XI in FIG. 9.
Figure 11B:
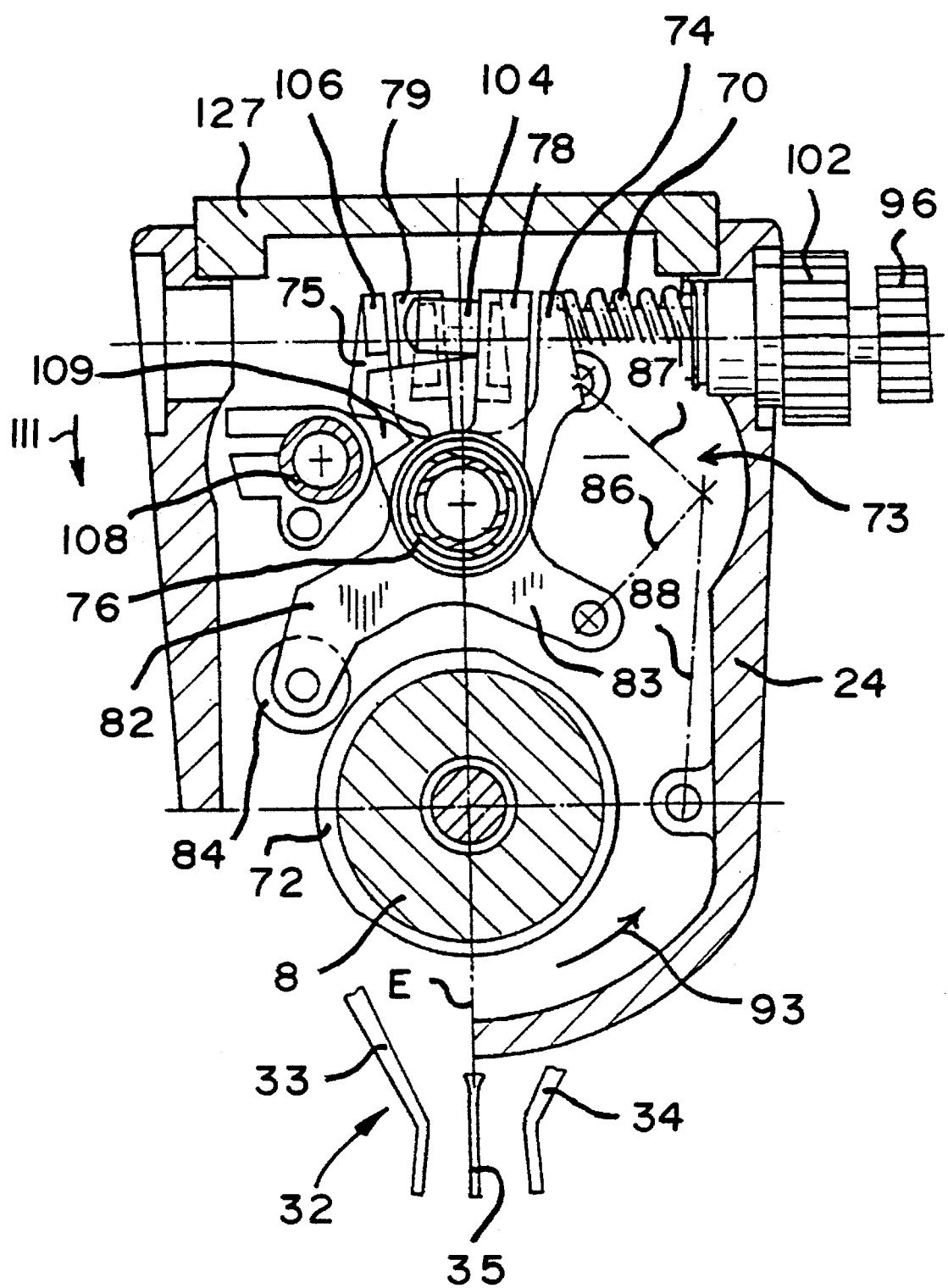
FIG. 11b is a cross-sectional view similar to that of FIG. 11a but depicting two legs of a forceps in an open position; 9.
Figure 12:
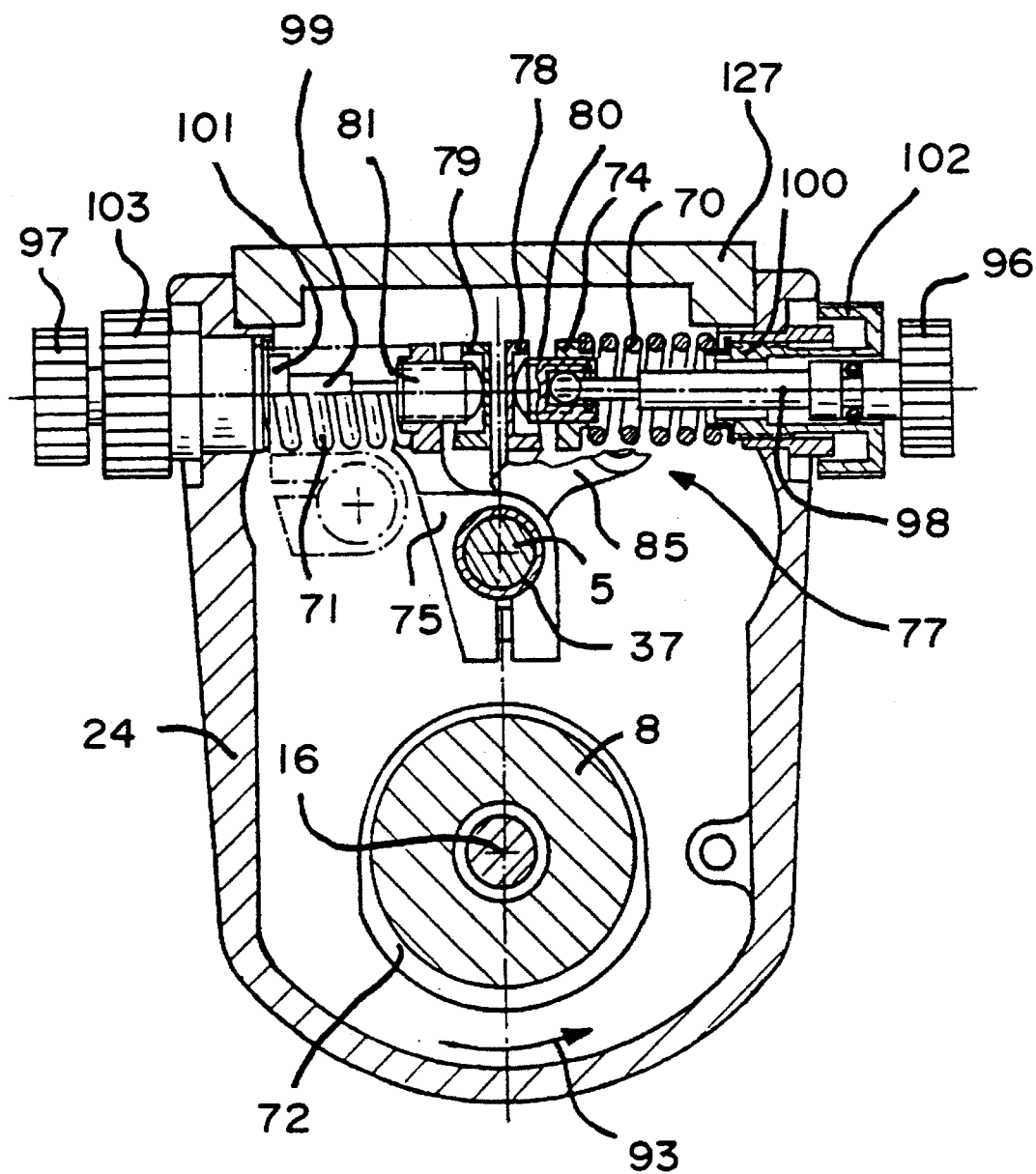
FIG. 12 is a cross-sectional view generally taken along line XII—XII in FIG. 9.
Figure 13:
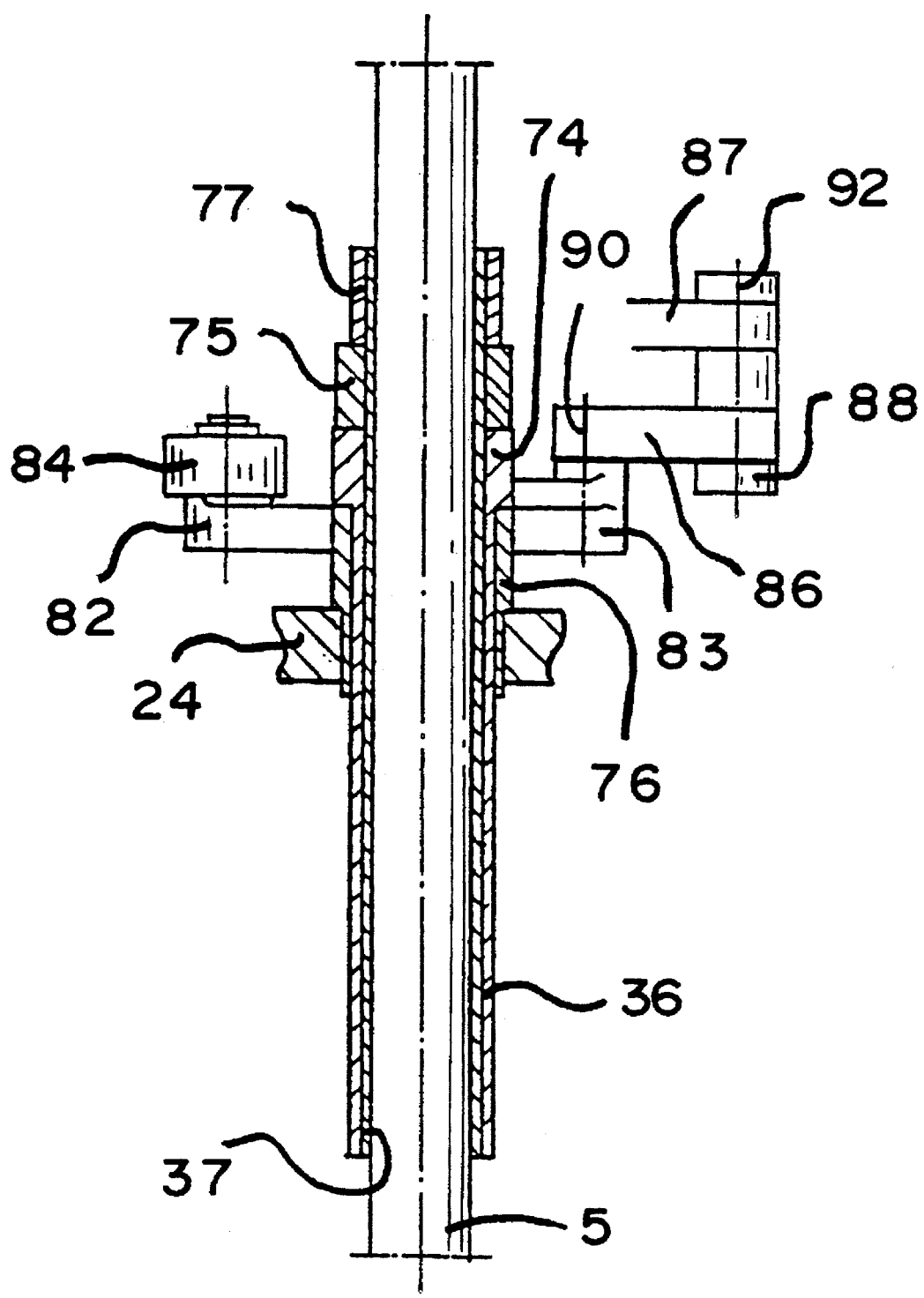
Figure 14:
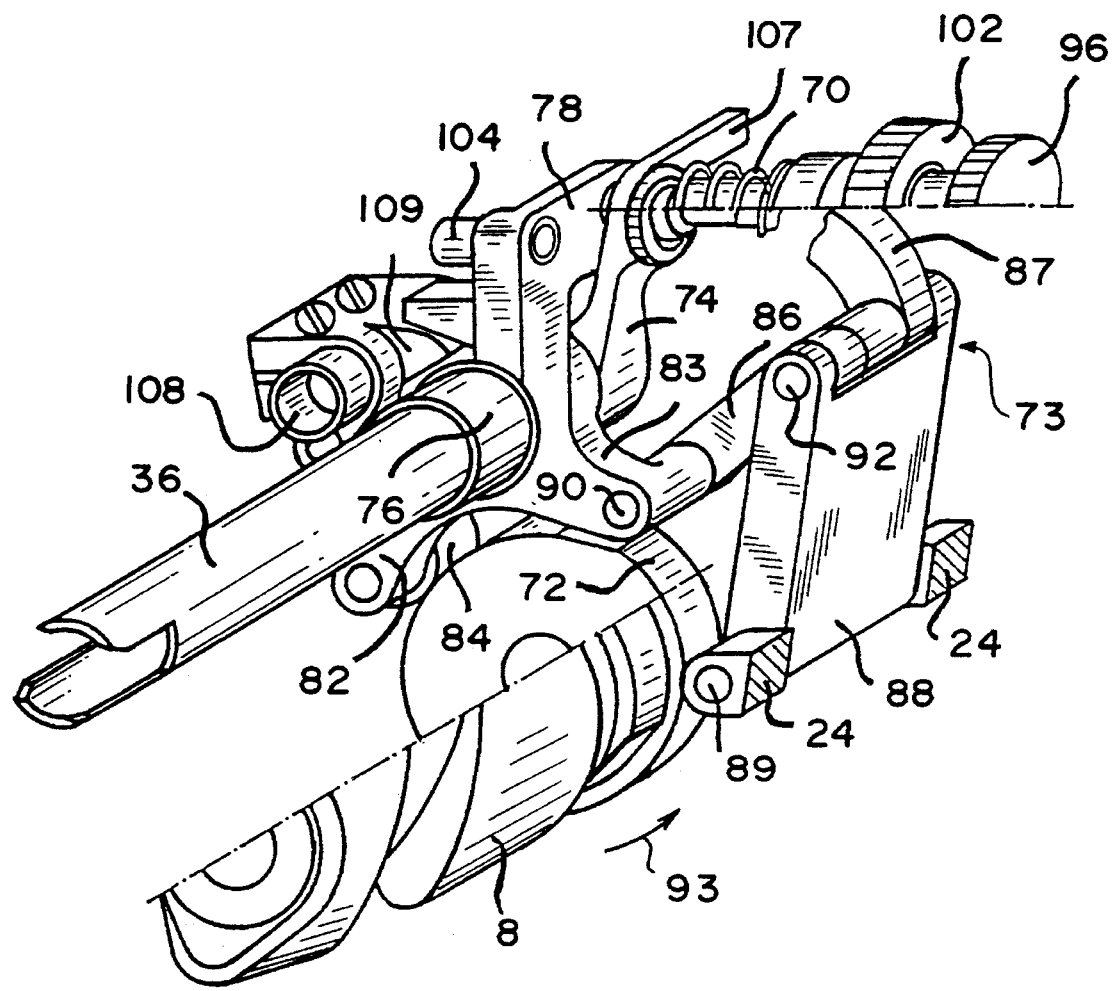
FIG. 14 is a perspective view of two drive levers associated with a forceps leg shown in FIGS. 11a, 11b and 12.
Figure 15:
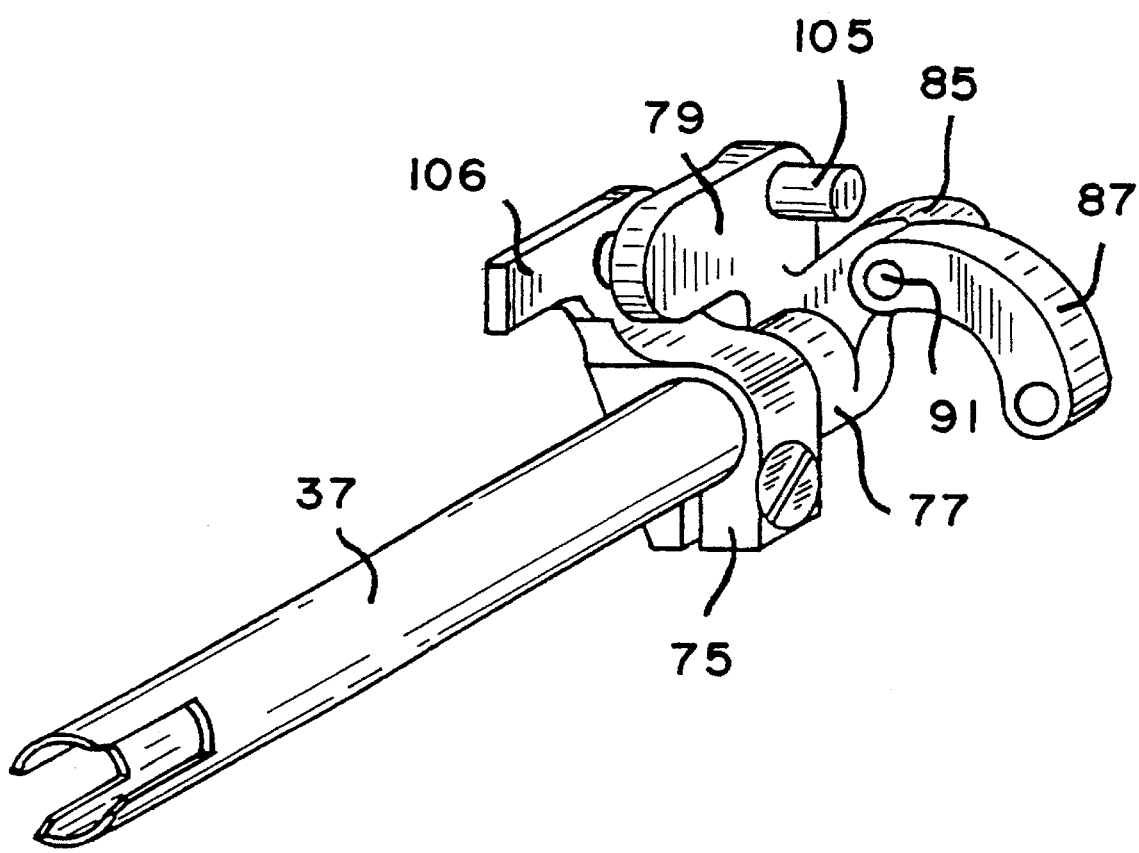
FIG. 15 is a perspective view of two drive levers for another forceps leg shown in FIGS. 11a, 11b and 12.

With respect to FIGS. 9–11a and 12–15, legs 33, 34 of forceps 32 are shown in their closed position from which, upon rotation of control roller 8 in the direction of arrow 93, are pivoted into their open position shown in FIG. 11b by arrows 94 and 95. In the process, control cam 72 of control roller 8 pivots second drive lever 76 associated with right forceps leg 33. Lever 76, in turn, drives by means of linkage 73 the second drive lever 77 associated with the left forceps leg 34, which thereby is rotated in the opposite direction through the same angle. The second drive levers 76, 77 each drive an associated first drive lever 74, 75 by means of pressure pin 80, 81 screwed into the first drive lever 74, 75 to change and adjust the closed position $S_r$ and $S_l$ of the right forceps leg 33 or of the left forceps leg 34. Such inward displacement increases the distance between the right forceps leg 33 and left forceps leg 34 from stationary middle arm 35. In turn, a outward screwing displacement would decrease this distance. The two pressure pins 80, 81 can be screwed by respective knobs 96, 97 into a corresponding shank 98, 99 acting on pressure pin 80, 81.

Helical compression springs 70, 71 each abut, at an end away from associated first drive lever 74, 75, against a threaded bushing 100, 101 mounted coaxially with shanks 98, 99 of knobs 96, 97 for pressure pins 80, 81 of first drive levers 74, 75 respectively. Knobs 102, 103 threadably engage bushings 100, 101 respectively and can be threaded into the housing 24 in order to adjust the prestressing of the helical compression springs 70, 71.

The two second drive levers 76, 77 of right forceps leg 33 and left forceps leg 34 are each fitted with a pin-shaped stop member 104 and 105 adapted to be engaged by first drive levers 75 and 74 respectively of left and right forceps legs 34 and 33. The stop members 104 and 105 each extend transversely to the outer and inner shafts 36 and 37 from the upper arms 78, 79 of the second drive lever 76, 77 toward a lateral tab 106, 107 of first drive lever 75, 74. For the closed position of forceps legs 33, 34, stops 104, 105 come to rest against an associated tab 106, 107 in order to set the spacing between second drive lever 76 of right forceps leg 33 and first drive lever 75 of left forceps leg 34, and between second drive lever 77 of left forceps leg 34 and first drive lever 74 of right forceps leg 33.

It then follows, in conjunction with linkage 73, that the particular angle assumed by upper arm 78, 79 of each second drive lever 76, 77 within the plane of symmetry E for the closed position of forceps legs 33, 34 and also the angle assumed by arm 82 of second drive lever 76 of right forceps leg 33 cooperating with control cam 72 within the plane of symmetry E in the closed position of forceps legs 33, 34, shall be reduced with an increase in the distance between forceps legs 33, 34 in the closed positions $S_r$, $S_l$ and the plane of symmetry E, i.e., the more deep the pressure pins 80, 81 in first drive levers 74, 75 are screwed in. The distance of roller 84 of arm 82 cooperating with control cam 72 from the axis of rotation of control roller 8 will decrease correspondingly, whereby the excursion by which control cam 72 can displace roller 84 during rotation of control roller 8 from the axis of rotation of roller 84 will commensurately increase, and thereby also the angle of pivoting of each forceps leg 33, 34 when forceps 32 are opened.

With reference to FIGS. 9–15, forceps 32 are shown in the state wherein pressure pins 80 and 81 are screwed in as deeply as possible, whereby forceps legs 33, 34 each are the greatest distance away from middle arm 35 when in the closed position of FIG. 11a, in which position roller 84 of second drive lever 76 of right forceps leg 33 rests against a lower peripheral segment of control cam 72. As a result, the total radial difference in height between the lower peripheral segment and the higher peripheral segment of control cam 72 is available to pivot second drive lever 76 as control roller 8 is rotating into the position of FIG. 11b. When relatively thin tissue edges must be sutured together, pressure pins 80, 81 in first drive levers 74, 75 are screwed outward to readjust the closed positions $S_r$, $S_l$ of forceps legs 33, 34 and to commensurately decrease their closed positions from stationary middle arm 35. In the process, roller 84 of second drive lever 76 is moved a corresponding distance away from the lower peripheral segment of control cam 72, whereby the angle about which the higher peripheral segment of control cam 72 pivots second drive lever 76 during the rotation of control roll 8 shall be correspondingly decreased.

An actuator shaft 108 is provided to lift forceps 32 and differs merely from actuator shaft 61 of the suturing apparatus of FIGS. 1–8 in that actuator shaft 108 is provided with a radial projection 109 for pivoting second drive lever 76 of right forceps leg 33. When actuator shaft 108 is rotated by means of handcrank 110 in the direction of arrow 111, it will indirectly pivot second drive lever 76 and second drive lever 77 of left forceps leg 34 by means of linkage 73 to spread apart both forceps legs 33, 34 against the opposing force of helical compression springs 70, 71.

Advancing tongs 120 comprising right and left legs 121 and 122 are provided in the suturing apparatus of FIGS. 16–24 for the stepwise advancement of the tissue edges A, B in the direction of arrow 29. Right and left legs 121 and 122 operate in synchronization with the opening and closing of forceps 32. Advancing tongs 120 carry out two kinds of motion, on one hand a closing and opening motion and, on the other hand, an advance and retraction motion. Accordingly, tong legs 121, 122 are displaceable in a dual manner, namely in the first place between a closed position and an open position in order to grip and to release tissue edges A, B, and in the second place between an initial position and a final position in the direction of advancement 29 and opposite the direction of advancement 29 in order to move tissue edges A, B or to resume their initial position to carry out the next advance step. The closing and opening of advancing tongs 120, advance and return of advancing tongs 120 and the closing and opening of forceps 32 are synchronized such that tong legs 121, 122 will move from the initial position to the final position during each opening phase of forceps 32 and from the final position into the initial position during each closing phase of forceps 32.

Right tong leg 121 and left tong leg 122 are biased by a common helical compression spring 123 into the closed position and are displaceable by a control cam 124 provided on control roll 8 against the biasing force of the spring 123 into the open position. In addition, tong legs 121 and 122 are coupled to each other by a linkage 125. A reversible electric stepping motor 126 is provided to displace tong legs 121, 122 jointly in and against the direction of advance 29.

Electric stepping motor 126 is mounted on a cover 127 of the apparatus and, by means of bevel gearing 128 and power dividing gearing 129, drives two spindles 130, 131 affixed respectively to the right and left tong legs 121, 122. Gearing 128 comprises two meshing bevel gears 132, 133 respectively connected to the output shaft 134 of electric stepping motor 126 and the input shaft 135 of power dividing gearing 129. Power dividing gearing 129 consists of an input gear 136 connected to input shaft 135 and two output gears 137, 138 that respectively mesh with input gear 136 and with spindle 130 of right tong leg 121 or spindle 131 of left tong leg 122 respectively.

Spindles 130, 131 are mounted in an axially displaceable manner, respectively parallel to outer shaft 36 and inner shaft 37 of forceps 32, and are provided at their respective rear ends with an outer thread 139 and 140. Each spindle 130, 131 passes through a ring 141, 142 mounted in an axially fixed but rotatable manner in housing 24 and fitted with a corresponding inner thread 143 and 144 coaxial with output gears 137 and 138 respectively of power dividing gearing 129. Due to this arrangement, each spindle 130, 131 and its associated ring 141, 142 can be screwed into each other on account of their outer and inner threads, 139, 143 and 140, 144 engaging each other. This ensures that each to-and-fro rotation of rings 141, 142 by means of electric stepping motor 126 causes a corresponding axial reciprocation of spindles 130, 131. The right and left tong legs 121 and 122 each project substantially radially from front ends of spindles 130 and 131.

Spindles 130, 131 are pivotable to-and-fro by means of two to-and-fro rotatable pivot bushings 145, 146 in order to displace tong legs 121, 122 into the closed and opened positions. Each spindle 130, 131 is axially displaceable but non-rotatable inside pivot bushings 145, 146. Each spindle 130, 131 is equipped with two mutually diametrically opposite rollers 147 and 148 respectively received in two corresponding longitudinal slots 149 and 150 of associated pivot bushings 145 and 146 in order to enable the axial displacement of spindles 130 and 131.

Pivot bushings 145, 146 are each fitted with an essentially radially projecting drive lever 151 and 152 respectively. Helical compression spring 123 is mounted between drive levers 151 and 152. Moreover, each pivot bushing 145, 146 comprises an essentially radially projecting arm 153 and 154 provided with a cross-pin 155 and an elongated slot 156 at their respective ends. By means of cross-pin 155 and slot 156, arms 153, 154 engage one another to form linkage 125 ensuring that pivot bushings 145, 146, spindles 130, 131 and tong legs 121, 122 are pivotable solely about identical angles in relative opposite directions.

Drive lever 152 associated with left tong leg 122 cooperates by means of a second drive lever 157 with control cam 124. Second drive lever 157 comprises a tubular hub 158 rotatably supported in housing 24 through which passes spindle 131 of left tong leg 122. Furthermore, second drive lever 157 is fitted with two arms 159, 160. Arm 159 cooperates with first drive lever 152 and arm 160 cooperates by means of a roller 161 rotatably supported at a free end thereof with control cam 124. Arms 159, 160 project substantially radially from hub 158. More specifically, arm 159 that cooperates with first drive lever 152 is mounted on a side of first drive lever 152 which is away from helical compression spring 123 and cooperates with lever 152 by means of a pressure pin 162 externally resting against first drive lever 152 and screwable into arm 159 in order to allow changing and adjusting of the closed positions $S_r'$, $S_l'$ of tong legs 121, 122.

The prestressing of helical compression spring 123 can also be changed and adjusted. For that purpose, helical compression spring 123 cooperates with drive lever 151 associated with right tong leg 121 by means of a pressure pin 163 threadable into lever 151. When pressure pin 163 in drive lever 151 is screwed inward, the prestressing of helical compression spring 123 is increased. If screwed outward, the prestressing decreases.

The two pressure pins 162, 163 are each screwed in-and-out by means of a respective drive knob 164 and 165, each of which must be pressed against the force of a helical compression spring (not shown) to link it to pressure pin 162 or 163 in a manner similar to the case for drive knobs 58, 59 of the suturing apparatus of FIGS. 1–8.

Figure 16:
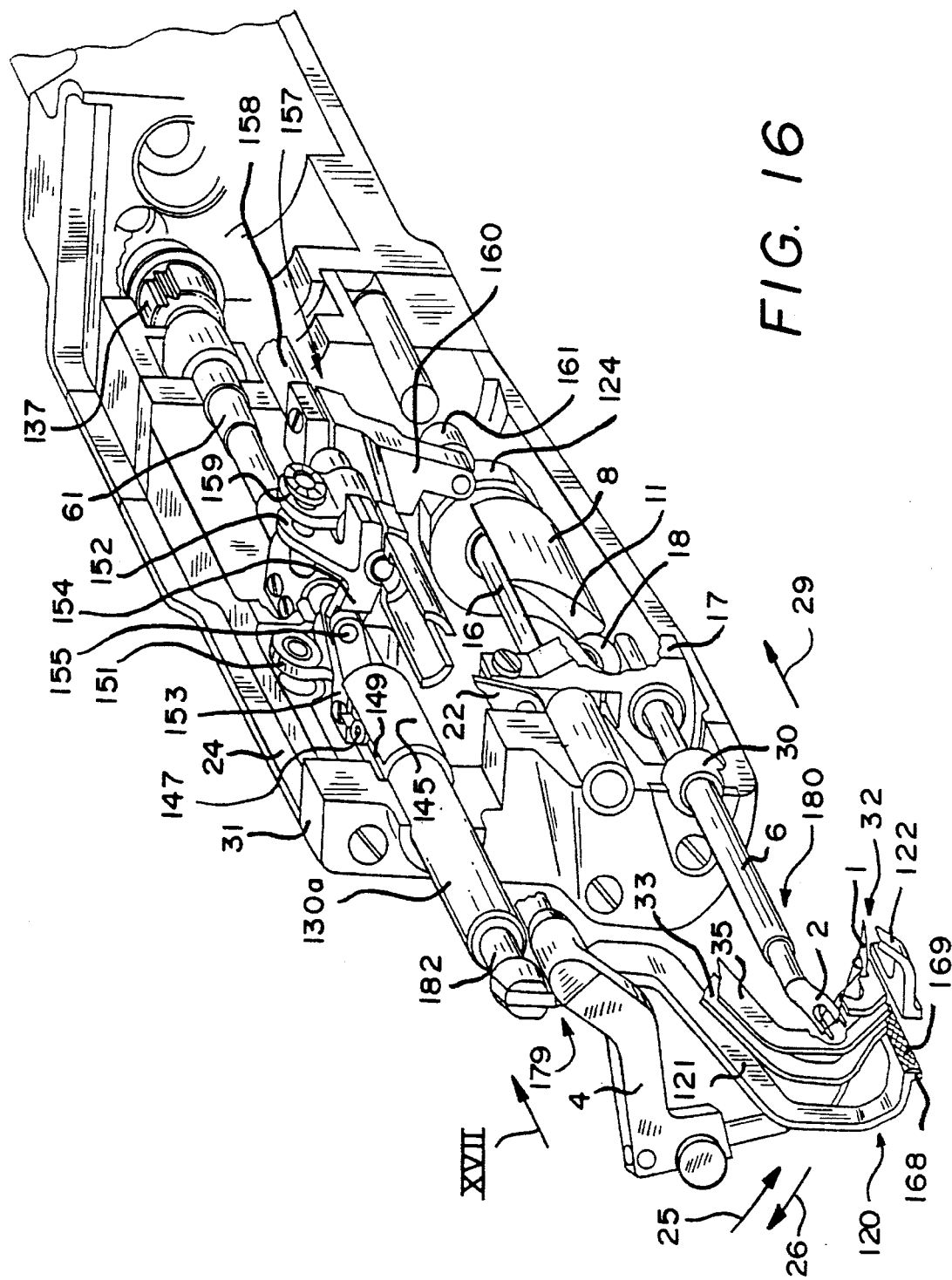
FIG. 16 is a partial perspective view similar to that of FIG. 1 but depicting a third embodiment of the invention.
Figure 17:
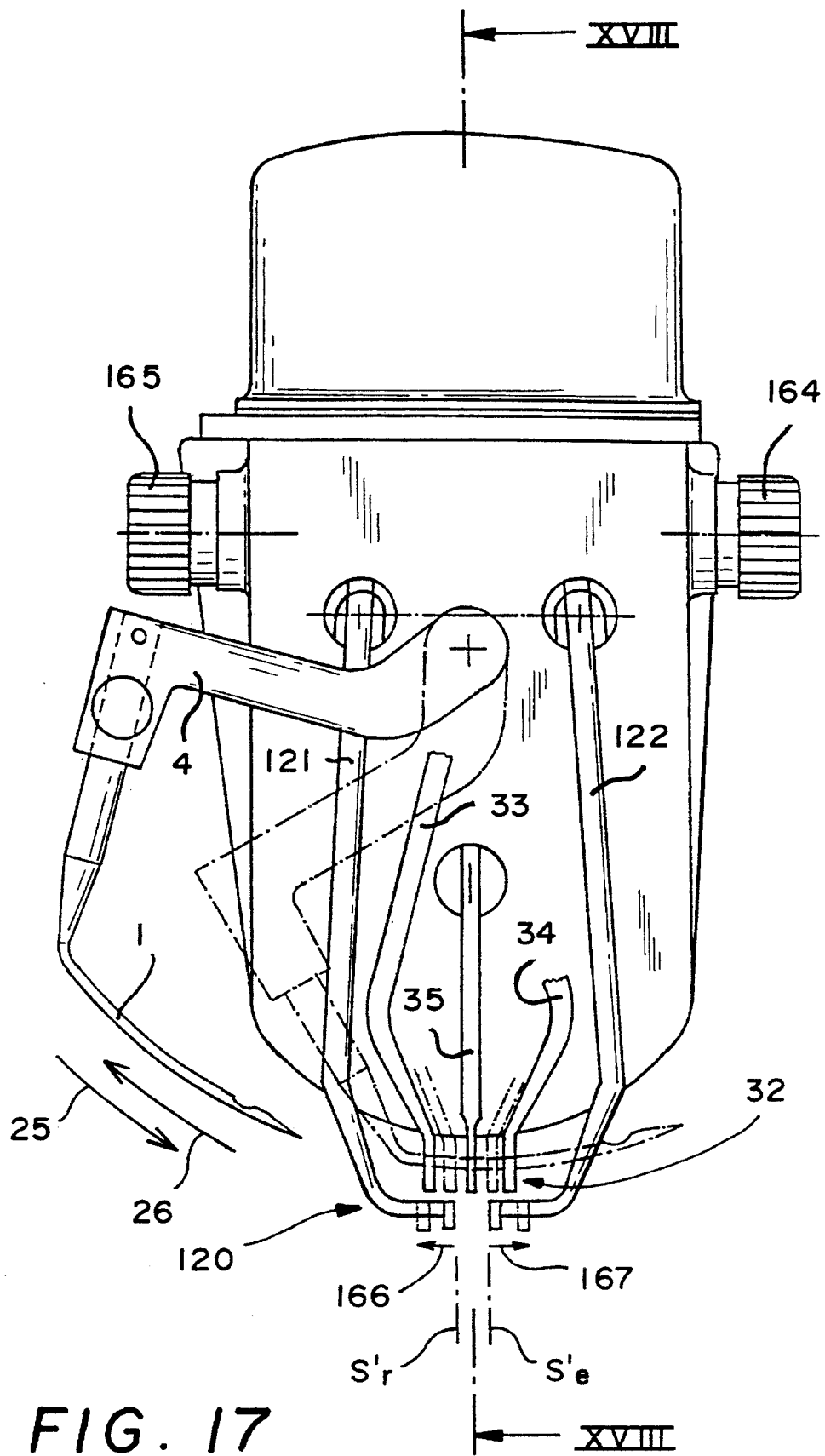
FIG. 17 is an enlarged front view generally taken in the direction of arrow XVII of FIG. 16.
Figure 18:
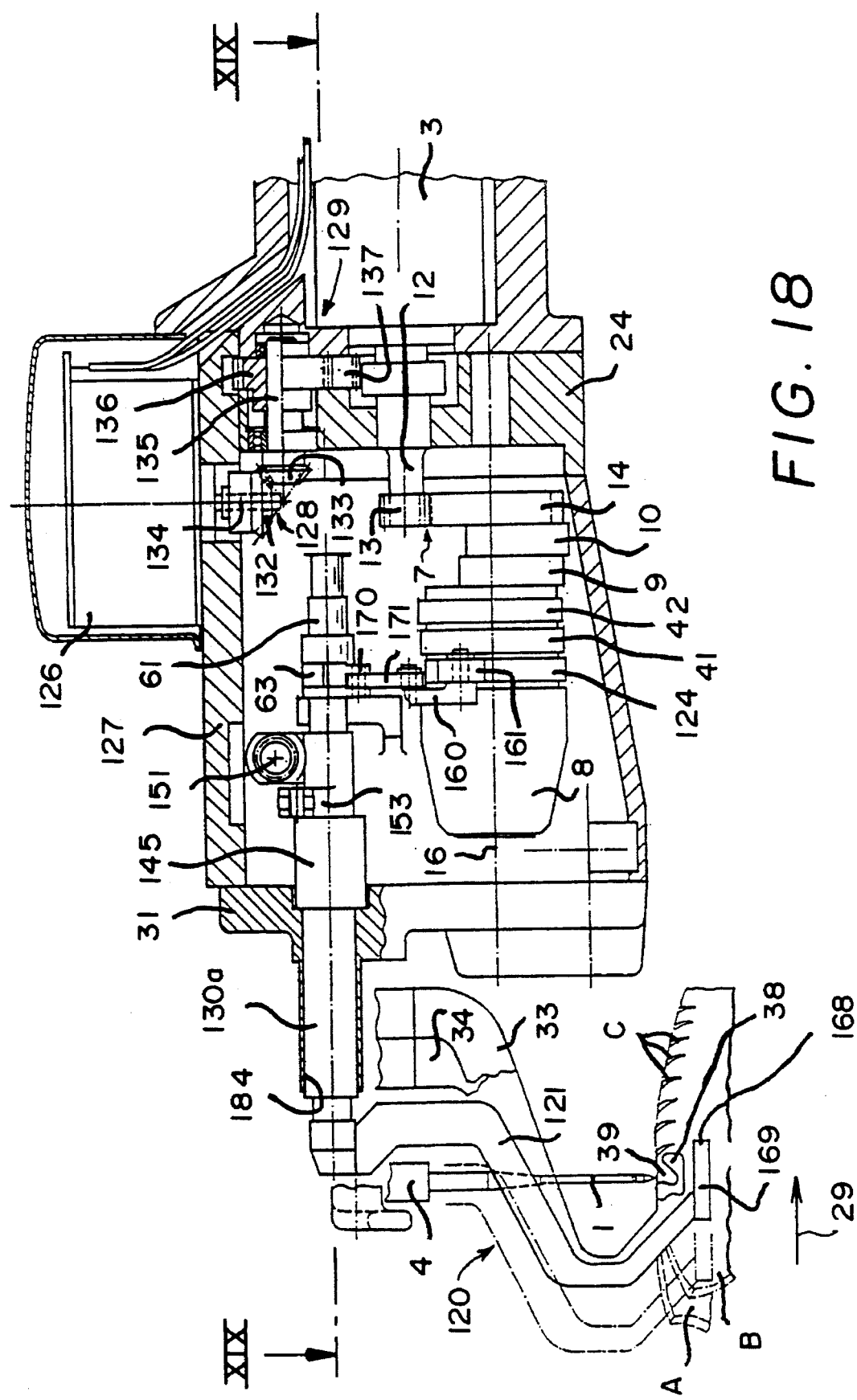
FIG. 18 is a cross-sectional view taken along line XVIII—XVIII of FIG. 17 on the scale of FIG. 16.
Figure 19:
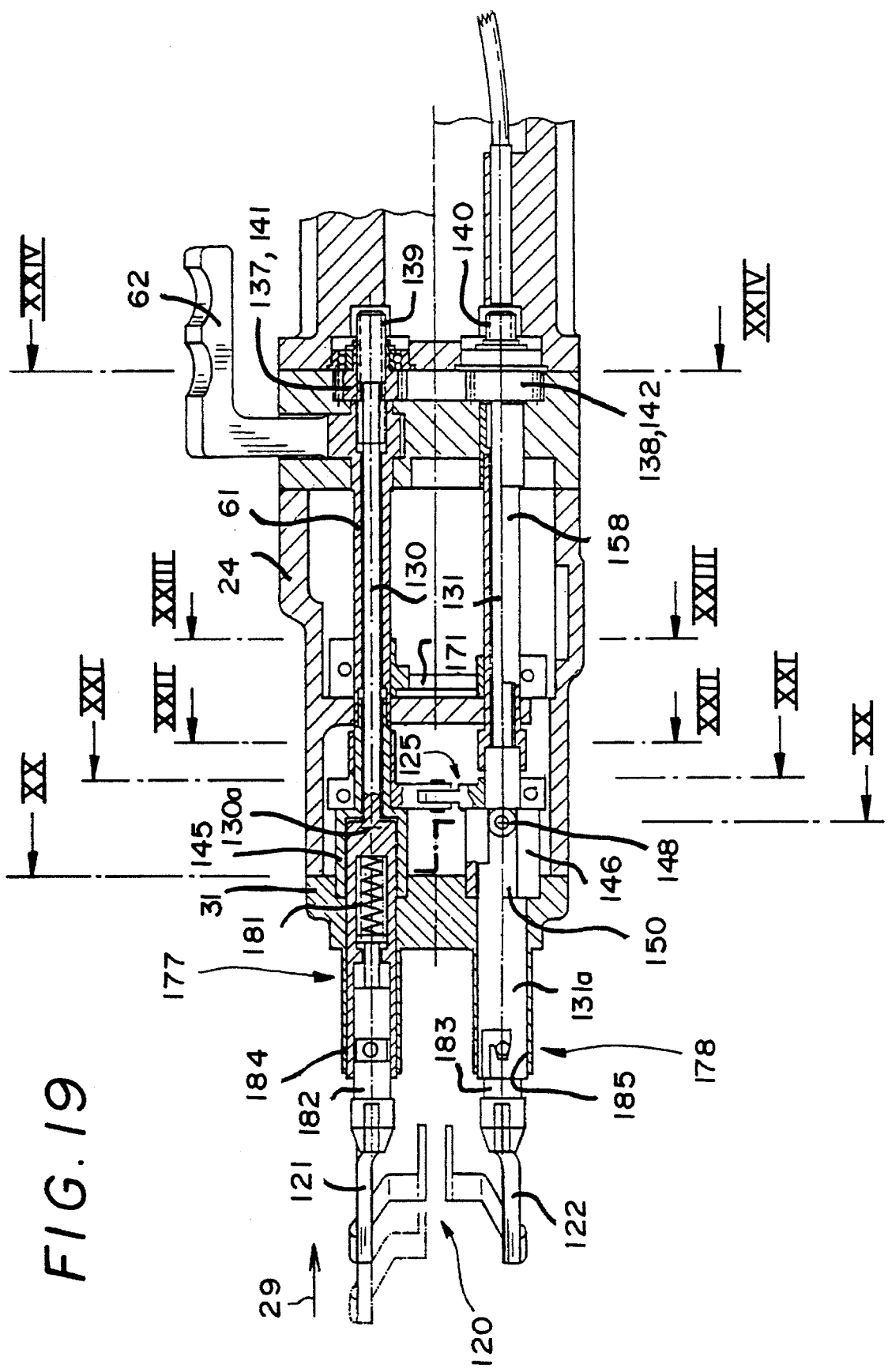
FIG. 19 is a cross-sectional view taken along line XIX—XIX of FIG. 18.
Figure 20:
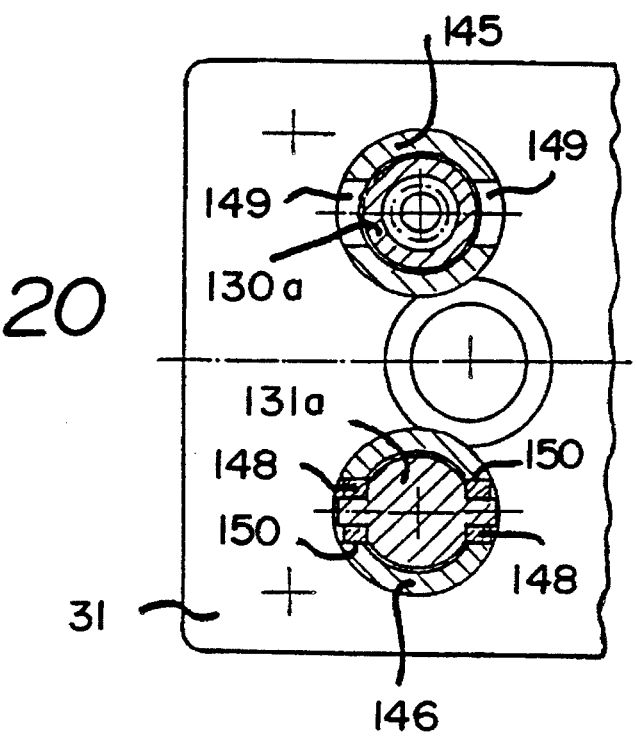
FIG. 20 is a cross-sectional view taken along line XX—XX of FIG. 19 on the scale of FIG. 17.
Figure 21:
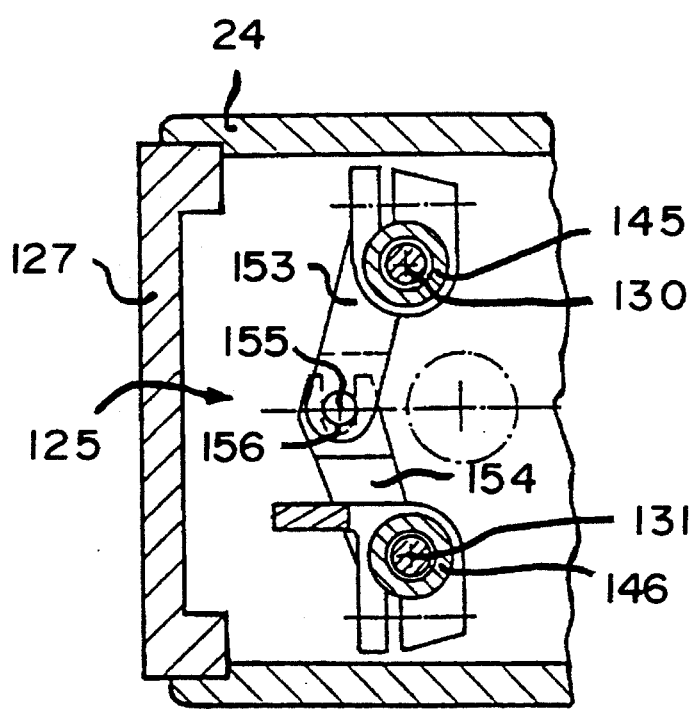
FIG. 21 is a cross-sectional view taken along line XXI—XXI of FIG. 19 on the scale of FIG. 17.
Figure 22:
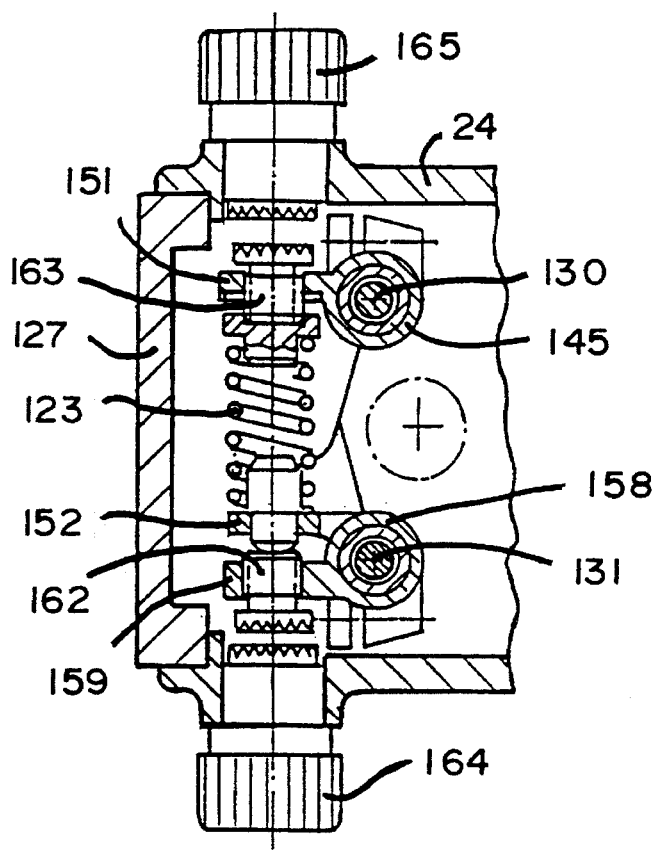
FIG. 22 is a cross-sectional view taken along line XXII—XXII of FIG. 19 on the scale of FIG. 17.
Figure 24:
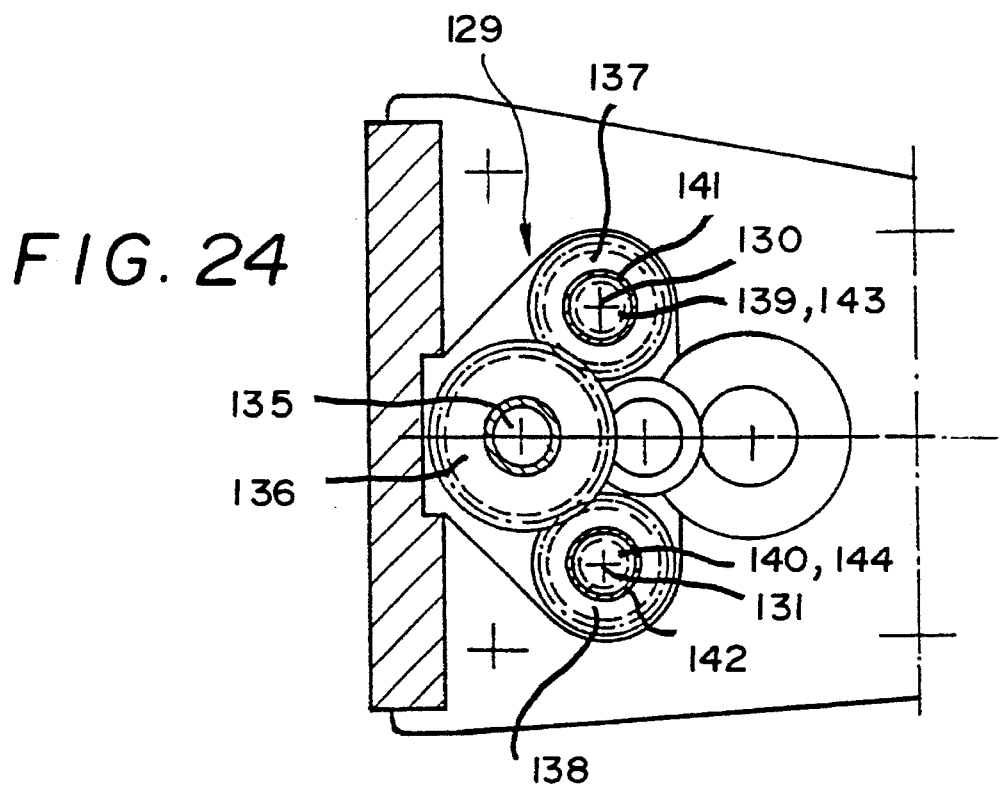
FIG. 24 is a cross-sectional view taken along line XXIV—XXIV of FIG. 19 on the scale of FIG. 17.
Figure 23:
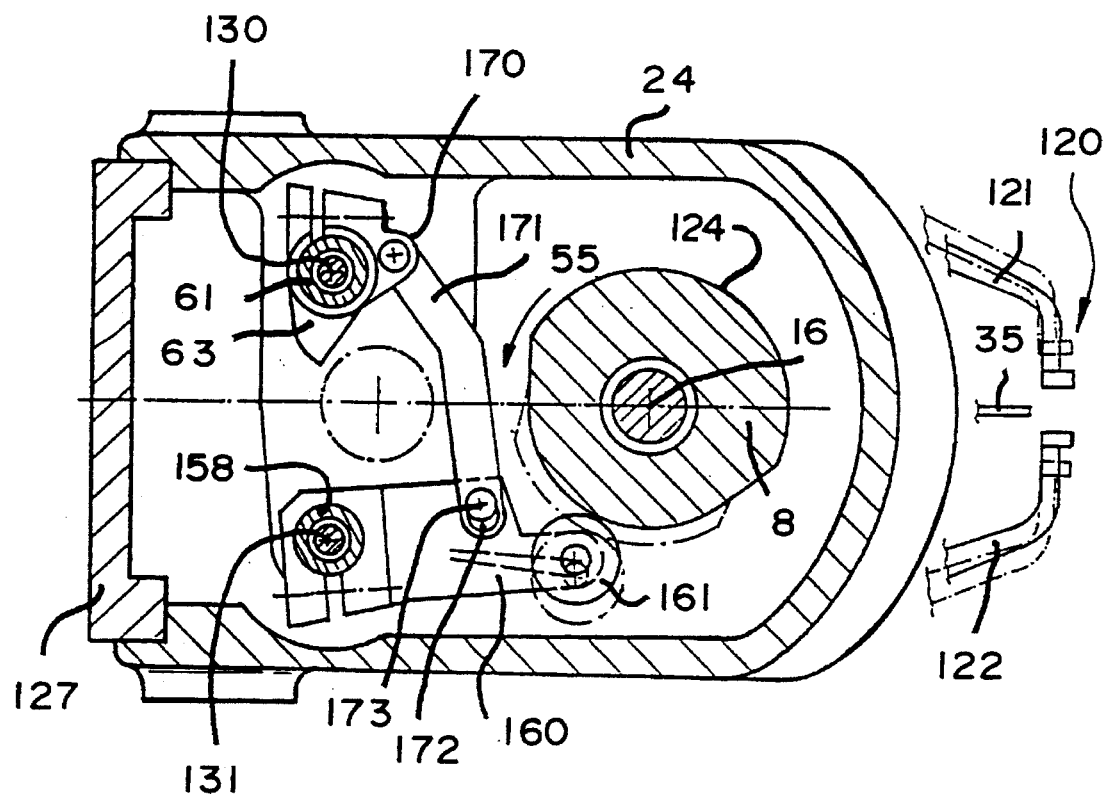
FIG. 23 is a cross-sectional view taken along line XXIII—XXIII of FIG. 19 on the scale of FIG. 17.

Referring to FIG. 16, arc needle 1 is shown pivoting in the direction of arrow 26 to exit tissue edges (not shown) that were sutured just previously and to return to a turn-around position as shown in solid lines in FIG. 17. The forked rocking gripper or loop catcher 2 moves correspondingly in the direction of arrow 28. Forceps 32 are closed, their legs 33, 34 are in the closed position. Advancing tongs 120 are open and are moving opposite the direction of advancement 29 into the initial position shown in dot-dash lines in FIGS. 18 and 19 wherein tong legs 121, 122, mounted and displaceable in a mirror-symmetrical manner relative to the plane of symmetry E, are pivoted into the closed position shown by solid lines in FIG. 17 in order to grip tissue edges A, B indicated by dot-dash lines in FIG. 18 directly beyond forceps 32, namely underneath presser feet 38 of forceps legs 33, 34 and also of the stationary middle arm 35.

After arc needle 1 exits the tissue edges, forceps 32 open and forceps legs 33, 34 pivot into the open position shown in solid lines in FIG. 17. Thereupon advancing tongs 120, of which legs 121, 122 are in the closed position, together with the gripped tissue edges move in the direction of advancement 29 into the end position shown in solid lines in FIGS. 18 and 19 wherein the advancing tongs 120 open again and tong legs 121, 122 pivot in the direction of the arrows 166, 167 into the open position indicated by the dot-dash lines in FIG. 17. The forceps 32 close again and forceps legs 33, 34 again pivot into the closed position indicated by dot-dash lines in FIG. 17 before arc needle 1, during the ensuing pivoting motion from the turn-around position shown in solid lines in FIG. 17, pierces the tissue edges in the direction of arrow 25, whereupon needle 1 moves into the turnaround position indicated by dot-dash lines.

The initial position of advancing tongs 120 and hence the length of the advance and return paths of these tongs between the initial and end positions, i.e., the stitching length of the suturing apparatus, is both changeable and adjustable. For that purpose, the control circuit of reversible electric stepping motor 126 is designed to allow changing and adjusting of the number of steps carried out by electric stepping motor 126 in either direction for each advance and retraction of tong legs 121, 122.

The two tong legs 121, 122 are each fitted at their free ends with a planar presser foot 168 which is adapted to engage an adjacent tissue edge. The design of the two presser feet 168 on their mutually facing sides 169 is such that, in the closed position of the tong legs 121, 122, any slippage between the gripped tissue edges and the presser feet 168 shall be substantially precluded. For instance, presser feet 168 may comprise spikes at sides 169 or be shaped in some other way to achieve a corresponding geometric locking arrangement with the tissue edges. Moreover, they may be coated with a suitable material to achieve corresponding friction with the tissue edges. When the tong legs 121, 122 are in their end position, their presser feet 168 will be precisely underneath presser feet 38 of forceps legs 33, 34 and stationary middle arm 35 in the manner best shown in FIG. 18.

Advancing tongs 120 and forceps 32 are lifted jointly by means of actuator shaft 61 that cooperates for this purpose with second drive lever 157 of left tong leg 122 to spread apart tong legs 121, 122 against the opposing force applied by helical compression spring 123. Actuator shaft 61 is hollow, encloses spindle 130 of right tong leg 121 and comprises, in addition to projection 63 and first arm 64, a second arm 170 also projecting substantially radially and cooperating by means of a pressure bracket 171 with arm 160 on a side of control cam 124 of the second drive lever 157. Pressure bracket 171, linked to second arm 170 at one end thereof, comprises an elongated slot 172 at its other end which receives a pin 173 carried by arm 160 of second drive lever 157. The elongated slot 172 allows pivoting of second drive lever 157 to-and-fro when the associated control cam 124 of the control roll 8 is rotated in the direction of the arrow 55, without thereby affecting actuator shaft 61 when handcrank 62 is in the rest position.

For purposes of sterilization, forceps legs 33, 34, stationary middle arm 35, tong legs 121, 122, needle lever 4 and loop catcher 2 can be readily removed by means of respective bayonet-type quick-disconnect connections 174–180 on outer and inner shafts 36, 37, apparatus front wall 31, right and left spindles 130, 131, needle shaft 5 and gripper rod 6 respectively.

The quick-disconnect units 177, 178 for tong legs 121, 122 are each respectively constituted by a coupling pin 182, 183 of tong legs 121, 122 and a front bush-like segment 130a, 131a of substantial diameter relative to that of associated spindle 130, 131, with segment 130a, 131a receiving coupling pin 182, 183 and a helical compression spring 181 and being supported in rotatable and axially displaceable manner in a comparatively long bore hole 184, 185 of corresponding diameter in the apparatus front wall 31. Each spindle section 130a, 131a is enclosed by an associated pivot bushing 145, 146 supported in rotational but axially stationary manner in housing 24.

With respect to the suturing apparatus depicted in FIGS. 1–8, two circular advancing discs 186, 187 are provided for the step-wise advance of tissue edges A, B in the direction of arrow 29 instead of advancing tongs 120. Discs 186, 187 are driven, similar to spindles 130, 131, by an electric stepping motor 188 mounted on the apparatus housing cover 127 and through associated bevel and power-dividing gearing in order to rotate intermittently in the direction of arrows 189, 190 of FIG. 2. The electric stepping motor 188 need not be reversible. The power dividing gearing operates directly in concert with two shafts to drive them in two mutually opposite directions. The shafts extend inside the apparatus housing 24 in a manner similar to the case for spindles 130, 131 and each cooperates by a bevel gear 191 with the right and left advancing discs 186, 187 respectively. In a manner similar to that of tong legs 121, 122, advancing discs 186, 187 are mutually spring-loaded and also may be lifted, against the biasing spring force. The housing of each bevel gearing 191 is rotatably supported in front wall 31 of housing 24. Again, each bevel gearing 191 is preferably connected in a readily detachable manner by a bayonet-type connector at its input side to the associated drive shaft in housing 24 to permit removing each advancing disc 186, 187 together with the particular bevel gearing 191 for purposes of sterilization.

Although described with respect to preferred embodiments of the invention, it should be readily understood that various changes and/or modifications may be made to the invention as described without departing from the spirit thereof, In general, the invention is only intended to be limited by the scope of the following claims.

We claim:

1. An apparatus for suturing together tissue edges comprising:

a housing:

an arc needle movably mounted to said housing for repetitively piercing tissue edges to be sutured;

a loop catcher attached to said housing;

means mounted in said housing for oscillating said arc needle and said loop catcher through respective arcuate paths in a synchronized manner in order to form stitches;

tissue edge bracing means mounted to said housing and including forceps having first and second legs; and means, mounted in said housing and connected to said forceps, for shifting said first and second legs, in synchronization with the oscillation of said arc needle, between a closed position wherein said first and second legs are adapted to clamp tissue edges to be sutured prior to the tissue edges being pierced by said arc needle and an open position wherein said first and second legs release the tissue edges following an ensuing exit of said arc needle from the tissue edges.

2. A suturing apparatus as claimed in claim 1, wherein said shifting means includes spring means for biasing said first and second legs into said closed position and cam means for shifting said first and second legs into said open position against the biasing of said spring means.

3. A suturing apparatus as claimed in claim 2, wherein said spring means comprises a common spring biasing both of said first and second legs towards said closed position.

4. A suturing apparatus as claimed in claim 3, further including means acting on said spring and at least one of said first and second legs for adjustably prestressing said spring.

5. A suturing apparatus as claimed in claim 3, wherein said spring is a helical compression spring.

6. A suturing apparatus as claimed in claim 2, wherein said spring means comprises first and second springs for respectively biasing said first and second legs into said closed position.

7. A suturing apparatus as claimed in claim 6, further comprising means acting on each of said first and second springs and each of said first and second legs for adjustably prestressing each of said first and second springs.

8. A suturing apparatus as claimed in claim 6, wherein each of said first and second springs constitutes a helical compression spring.

9. A suturing apparatus as claimed in claim 2, wherein said cam means comprises first and second control cams for respectively shifting said first and second legs into said open position.

10. A suturing apparatus as claimed in claim 9, wherein said oscillating means includes a control roller for driving said arc needle and said loop catcher, said first and second control cams being provided on said control roller.

11. A suturing apparatus as claimed in claim 2, wherein said shifting means includes a transmission assembly coupling said first and second legs.

12. A suturing apparatus as claimed in claim 11, wherein said oscillating means includes a control roller for driving said arc needle and said loop catcher, said cam means including a control cam carried by said control roller.

13. A suturing apparatus as claimed in claim 1, wherein said shifting means includes means for adjusting the closed position of said first and second legs.

14. A suturing apparatus as claimed in claim 11, wherein said transmission assembly includes a pair of first drive levers connected to said first leg and a pair of second drive levers connected to said second leg, said pairs of first and second drive levers being interconnected by adjusting members.

15. A suturing apparatus as claimed in claim 14, wherein said spring means comprises a helical compression spring that biases each of said first and second legs towards said closed position, said helical compression spring being mounted between said pair of first drive levers and extending adjacent said second pair of drive levers, said adjusting members constituting pressure pins that engage said pair of first drive levers and which are threadably attached to said pair of second drive levers.

16. A suturing apparatus as claimed in claim 14, wherein said spring means comprises two helical compression springs each of which biases a respective one of said first and second legs to said closed position, said springs being positioned outside of said pair of first drive levers within which extend said pair of second drive levers, said adjusting members constituting pressure pins externally engaging said pair of second drive levers and threadably attached to said pair of first drive levers.

17. A suturing apparatus as claimed in claim 14, wherein said cam means includes first and second control cams, each of said pair of second drive levers being formed with a first arm carried by one of said pair of first drive levers and a second arm that engages a respective one of said first and second control cams.

18. A suturing apparatus as claimed in claim 14, wherein each of said pair of second drive levers is formed with a first arm for cooperation with an associated one of said pair of first drive levers, one of said second drive levers being attached to a third arm that engages said control cam.

19. A suturing apparatus as claimed in claim 14, further comprising at least one stop member positioned between an associated pair of said pairs of first and second drive levers.

20. A suturing apparatus as claimed in claim 19, wherein said shifting means causes said pair of second drive levers to move along identical paths of motions but in opposite directions relative to a plane of symmetry fixed relative to the apparatus.

21. A suturing apparatus as claimed in claim 1, further comprising a hollow outer shaft and an inner shaft received in said outer shaft, said outer and inner shafts being mutually pivotable, each of said outer and inner shafts being attached to a first end of a respective one of said first and second legs.

22. A suturing apparatus as claimed in claim 14, further comprising a hollow outer shaft and an inner shaft received in said outer shaft, said outer and inner shaft being mutually pivotable, each of said outer and inner shafts being attached to a first end of a respective one of said first and second legs and a second end of each of said first and second legs being attached to a respective one of said pair of first drive levers.

23. A suturing apparatus as claimed in claim 22, wherein one of said pair of second drive levers is mounted on said outer shaft and the other of said pair of second drive levers is rotatably mounted on said inner shaft.

24. A suturing apparatus as claimed in claim 23, further comprising a rotatable actuator shaft extending parallel to said outer and inner shafts and serving to lift said forceps by shifting said pair of second drive levers, and a handcrank attached to said actuator shaft whereby movement of said handcrank causes said first and second legs to spread apart.

25. A suturing apparatus as claimed in claim 24, wherein said actuator shaft is provided with a pair of radially projecting arms adapted to engage and pivot a respective one of said pair of second drive levers, one of said arms being connected by a bracket to the second drive lever associated with the other of said arms.

26. A suturing apparatus as claimed in claim 24, wherein said actuator shaft comprises a radially projecting arm adapted to engage and pivot one of said pair of second drive levers.

27. A suturing apparatus as claimed in claim 23, wherein said transmission assembly includes two transmission side arms each of which is linked by a connection bracket to one end of a pivot lever which is pivotable at its other end about a shaft that extends parallel to both the outer and inner shafts.

28. A suturing apparatus as claimed in claim 21, wherein said arc needle is carried by a needle shaft that passes through said inner shaft.

29. A suturing apparatus as claimed in claim 21, further comprising quick-disconnect means interconnecting said first and second legs to said outer and inner shafts respectively.

30. A suturing apparatus as claimed in claim 1, wherein said tissue edge bracing means comprises a planar presser foot carried by an end of each of said first and second legs for engaging an edge of a tissue to be sutured, each said presser foot including a recess through which said arc needle passes.

31. A suturing apparatus as claimed in claim 1, wherein said forceps further include a stationary middle arm that cooperates with said first and second legs to hold together tissue edges when in said closed position.

32. A suturing apparatus as claimed in claim 31, wherein the stationary middle arm is affixed by a quick-disconnect means to a front wall of the apparatus.

33. A suturing apparatus as claimed in claim 31, wherein the stationary middle arm includes a planar presser foot adapted to abut the tissue edges to be sutured, the presser foot of said stationary middle arm being formed with a recess through which said arc needle passes.

34. A suturing apparatus as claimed in claim 1, further comprising advancing tongs including two leg elements and means for operating said advancing-tongs, synchronously with the opening and closing of the first and second legs of said forceps, between a closed position to grip tissue edges to be sutured at a location adjacent the forceps and an open position to release the tissue edges.

35. A suturing apparatus as claimed in claim 34, further comprising at least one spring urging said leg elements into their closed position and at least one control cam for moving said leg elements into their open position.

36. A suturing apparatus as claimed in claim 35, wherein said leg elements are spring loaded by a common spring into their closed position.

37. A suturing apparatus as claimed in claim 36, further comprising means acting on said spring and at least one of said leg elements for adjusting a loading force applied by said spring on said leg elements.

38. A suturing apparatus as claimed in claim 36, wherein said spring is a helical compression spring.

39. A suturing apparatus as claimed in claim 35, further comprising a linkage coupling said leg elements for movement to said open position in unison.

40. A suturing apparatus as claimed in claim 39, wherein said at least one control cam is formed on a control roller, said control roller comprising part of said means for oscillating said arc needle and said loop catcher.

41. A suturing apparatus as claimed in claim 34, wherein said means for operating said advancing tongs includes means for adjusting the closed position of said leg elements.

42. A suturing apparatus as claimed in claim 41, wherein said means for operating said advancing tongs includes a single drive lever attached to one of said leg elements and a pair of interconnected drive levers for the other of said two leg elements, said adjusting means acting on said pair of interconnected drive levers.

43. A suturing apparatus as claimed in claim 42, wherein said adjusting means comprises a pressure pin that rests externally against one of said pair of interconnected drive levers and which is threadably attached to the other of said pair of interconnected drive levers.

44. A suturing apparatus as claimed in claim 34, wherein said operating means comprises a reversible electric stepping motor.

45. A suturing apparatus as claimed in claim 44, wherein said electric stepping motor is adjustable.

46. A suturing apparatus as claimed in claim 44, further comprising a spindle carried by each of said leg elements and a ring connected to each spindle, each of said rings being adapted to be rotated to-and-fro by the electric stepping motor and being threadably secured by means of an inner thread onto an outer thread of a corresponding said spindle, such that rotation of each of said rings to-and-fro results in axial reciprocation of a respective said spindle.

47. A suturing apparatus as claimed in claim 46, further comprising a power divider assembly including an input gear driven by the electric stepping motor and two output gears, said output gears each meshing with the input gear and being connected to a respective one of said rings.

48. A suturing apparatus as claimed in claim 47, wherein each ring and its associated output gear are mutually coaxial and integrally formed.

49. A suturing apparatus as claimed in claim 47, further comprising bevel gearing positioned between the electric stepping motor and the power divider assembly.

50. A suturing apparatus as claimed in claim 49, wherein the bevel gearing consists of two mutually meshing conical gears respectively connected to an output shaft of the electric stepping motor and an input shaft of the power divider assembly.

51. A suturing apparatus as claimed in claim 46, wherein said spindles are pivotable to-and-fro by means of two rotatable pivot bushings, each said spindle being non-rotatably attached to a respective said pivot bushing while being axially displaceable therein.

52. A suturing apparatus as claimed in claim 51, wherein said means for operating said advancing tongs includes a pair of drive levers, each of said two pivot bushings being fitted with a respective one of said pair of drive levers.

53. A suturing apparatus as claimed in claim 52, further comprising a linkage including two arms projecting radially from a respective said pivot bushing, each of said arms including first ends attached to a respective one of said leg elements and second ends that are interconnected by means of a cross-pin.

54. A suturing apparatus as claimed in claim 52, wherein one of said pair of drive levers includes two arms projecting radially from a tubular hub mounted on the spindle which passes through the pivot bushing fitted with the first drive lever.

55. A suturing apparatus as claimed in claim 46, further comprising a hollow outer shaft and an inner shaft received in said outer shaft, said outer and inner shafts being mutually pivotable within said housing, each of said outer and inner shafts being attached to a respective one of said first and second legs, said spindles extending parallel to said outer and inner shafts, each of said two leg elements projecting radially from a respective one of said spindles.

56. A suturing apparatus as claimed in claim 54, further comprising a hollow actuator shaft rotatable by a handcrank, said actuator shaft being mounted on the spindle which runs parallel to the spindle extending through the pivot bushing fitted with the first drive lever, said actuator shaft further extending through the tubular hub of said second drive lever, said actuator shaft comprising a radially projecting arm that is connected by a pressure bracket to one of said arms in order to spread apart the leg elements of said advancing tongs when said actuator shaft is rotated by said handcrank.

57. A suturing apparatus as claimed in claim 46, further comprising quick-disconnect means connecting said two leg elements to respective ones of said spindles.

58. A suturing apparatus as claimed in claim 34, wherein each of said leg elements includes a planar presser foot at a free end thereof adapted to grip an edge of a tissue to be sutured, said apparatus further including means for preventing slippage between the gripped tissue edges and the two leg elements.

* * * * *